United States Patent
Ohnogi et al.

(10) Patent No.: US 7,498,357 B2
(45) Date of Patent: Mar. 3, 2009

(54) CHALCONE COMPOUNDS

(75) Inventors: Hiromu Ohnogi, Otsu (JP); Katsumi Sugiyama, Otsu (JP); Tatsuji Enoki, Otsu (JP); Eiji Kobayashi, Otsu (JP); Hiroaki Sagawa, Otsu (JP); Ikunoshin Kato, Otsu (JP)

(73) Assignee: Takara Bio Inc., Otsu-shi (JP)

( * ) Notice: Subject to any disclaimer, the term of this patent is extended or adjusted under 35 U.S.C. 154(b) by 47 days.

(21) Appl. No.: 10/581,034

(22) PCT Filed: Dec. 1, 2004

(86) PCT No.: PCT/JP2004/017887

§ 371 (c)(1),
(2), (4) Date: May 30, 2006

(87) PCT Pub. No.: WO2005/054170

PCT Pub. Date: Jun. 16, 2005

(65) Prior Publication Data

US 2007/0112066 A1    May 17, 2007

(30) Foreign Application Priority Data

Dec. 5, 2003    (JP)    ............... 2003-408215

(51) Int. Cl.
*A61K 31/343*    (2006.01)
*C07D 307/80*    (2006.01)

(52) U.S. Cl. ................... 514/470; 549/437

(58) Field of Classification Search ........... 514/470, 514/557, 719; 549/437; 562/400; 568/659, 568/702

See application file for complete search history.

(56) References Cited

U.S. PATENT DOCUMENTS

| 5,808,137 A | 9/1998 | Bombardelli et al. |
| 2003/0144316 A1 | 7/2003 | Ohnogi et al. |

FOREIGN PATENT DOCUMENTS

| EP | 1623704 A | 2/2006 |
| EP | 1656943 A | 5/2006 |
| JP | 63-104912 A | 5/1988 |
| JP | 64-13019 A | 1/1989 |
| JP | 2-164822 A | 6/1990 |
| JP | 4-29968 A | 1/1992 |
| JP | 10-511346 A | 11/1998 |
| JP | 2001-58969 A | 3/2001 |
| WO | WO-96/19209 A1 | 6/1996 |
| WO | WO-01/54682 A1 | 8/2001 |
| WO | WO-2004/96198 A1 | 11/2004 |
| WO | WO-2004/112817 A1 | 12/2004 |
| WO | WO-2005/074906 A1 | 8/2005 |

OTHER PUBLICATIONS

J.R. Dimmock, et al., Bioactivities of Chalcones, pp. 1125-1149.

*Primary Examiner*—Taofiq A Solola
(74) *Attorney, Agent, or Firm*—Birch, Stewart, Kolasch & Birch, LLP

(57) ABSTRACT

The present invention provides a novel chalcone compound, its derivative or a salt thereof, each having a suppressive action of NO production or an inhibitory action of aldose reductase. In addition, the present invention provides a medicament, a food, a beverage or a feed having a therapeutic or prophylactic effect for a disease showing sensitivity to the compound, by utilizing the physiological actions of the compound.

6 Claims, 9 Drawing Sheets

[Figure 1]
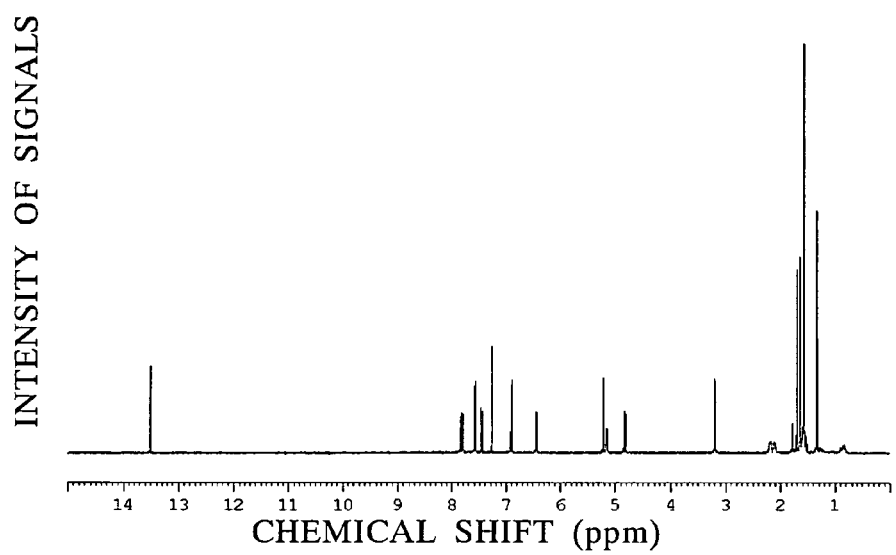
[Figure 2]
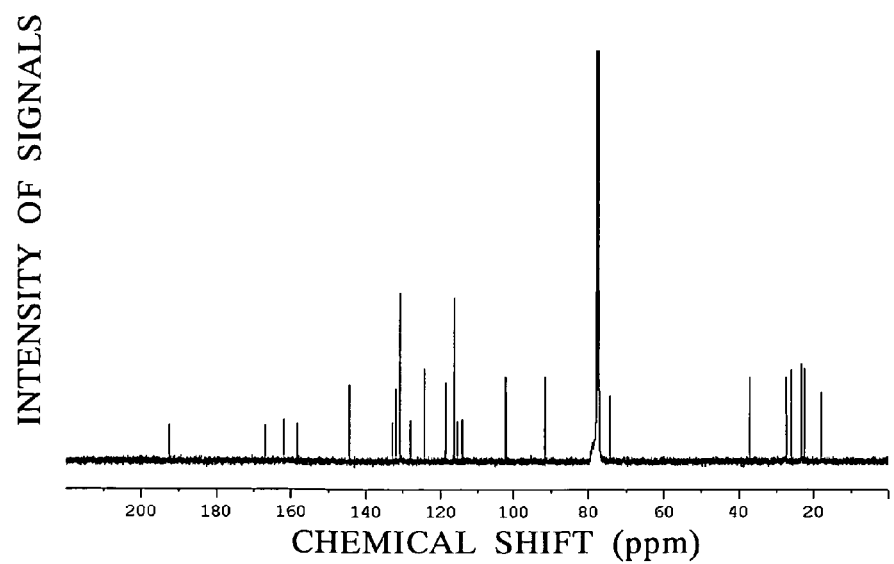

[Figure 3]
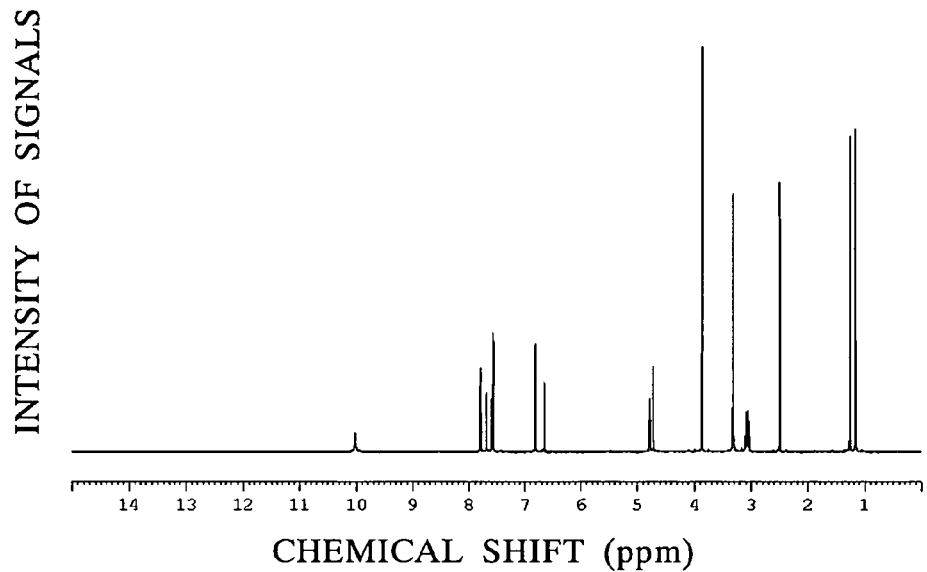
[Figure 4]
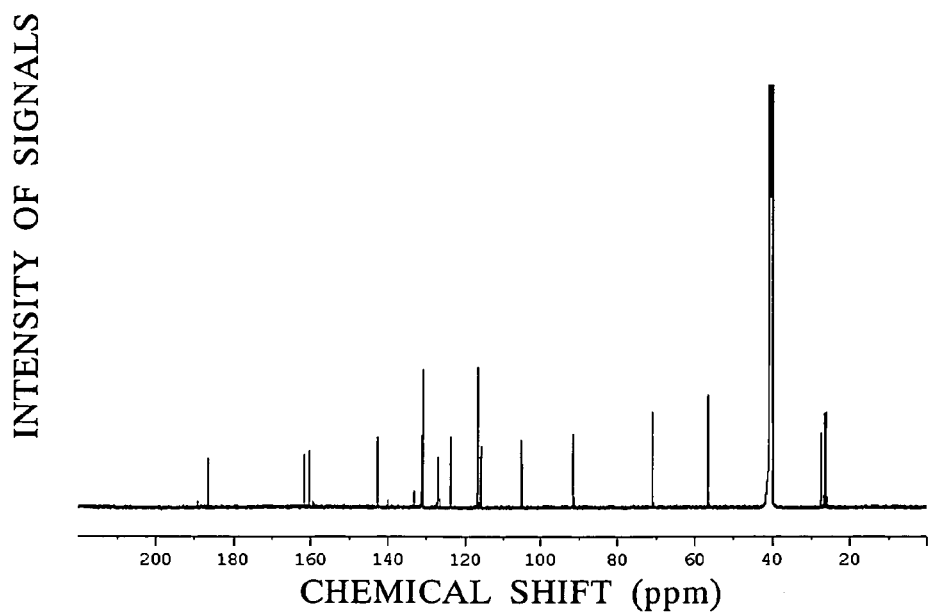

[Figure 5]
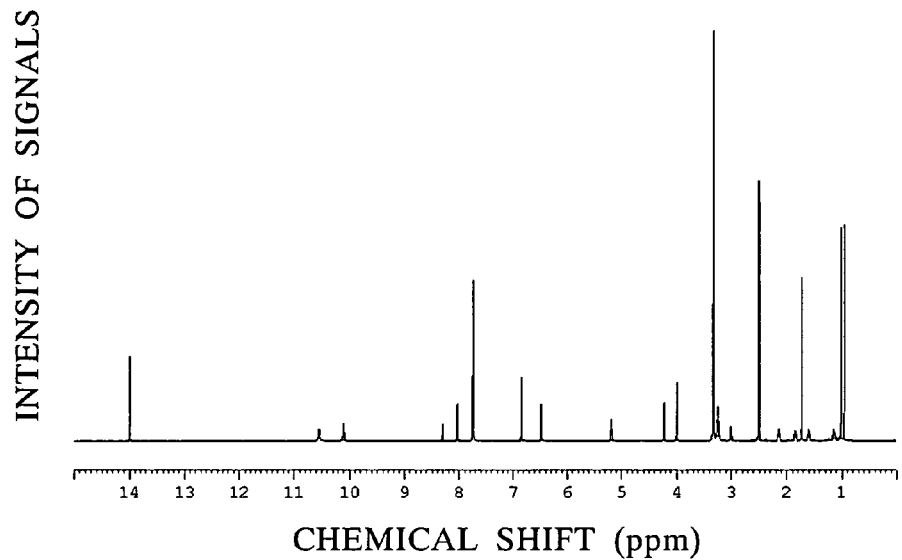
[Figure 6]
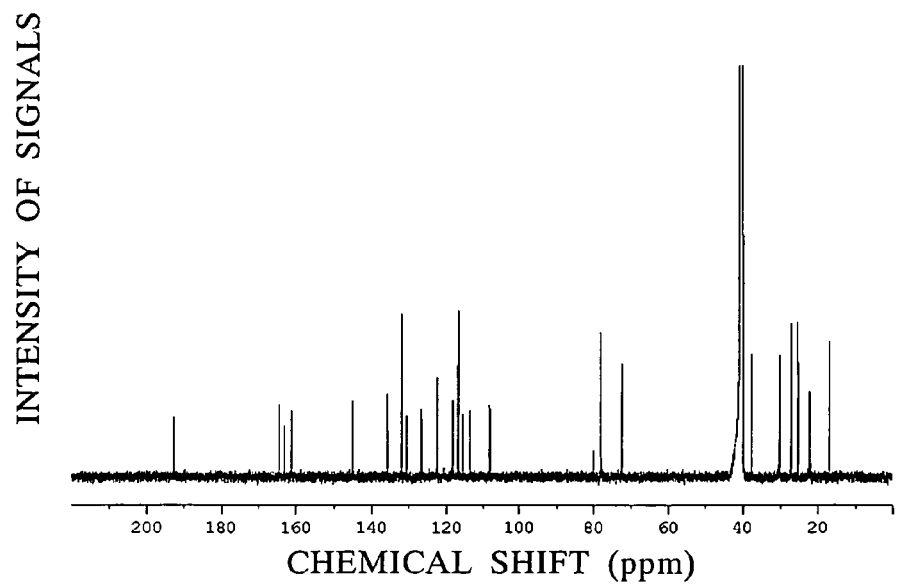

[Figure 7]
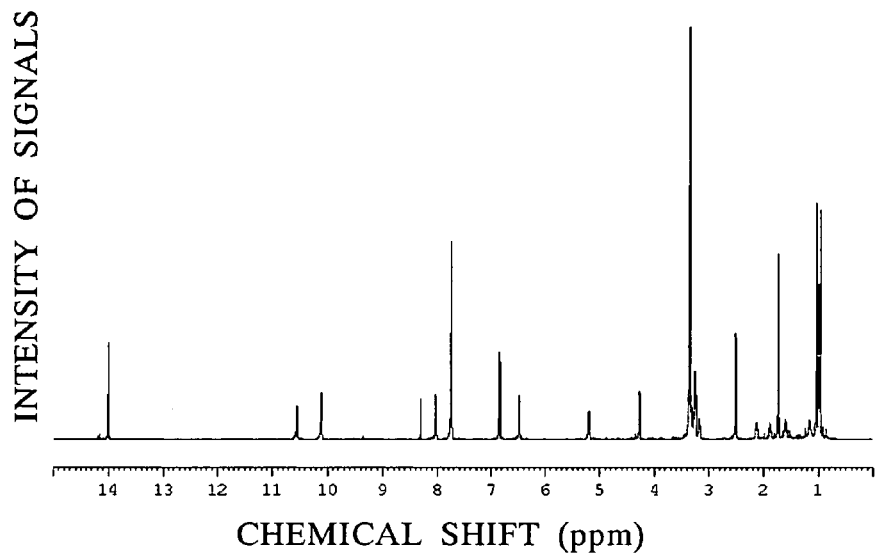
[Figure 8]
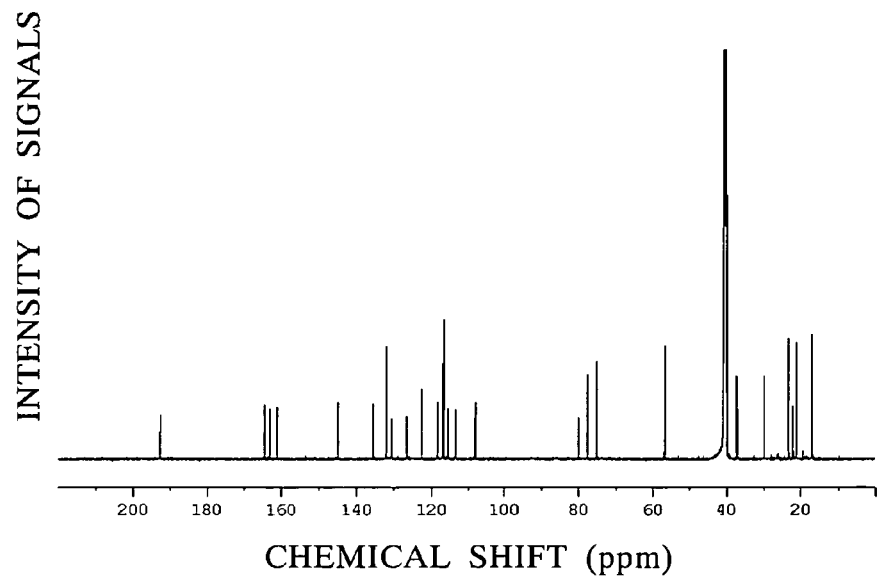

[Figure 9]
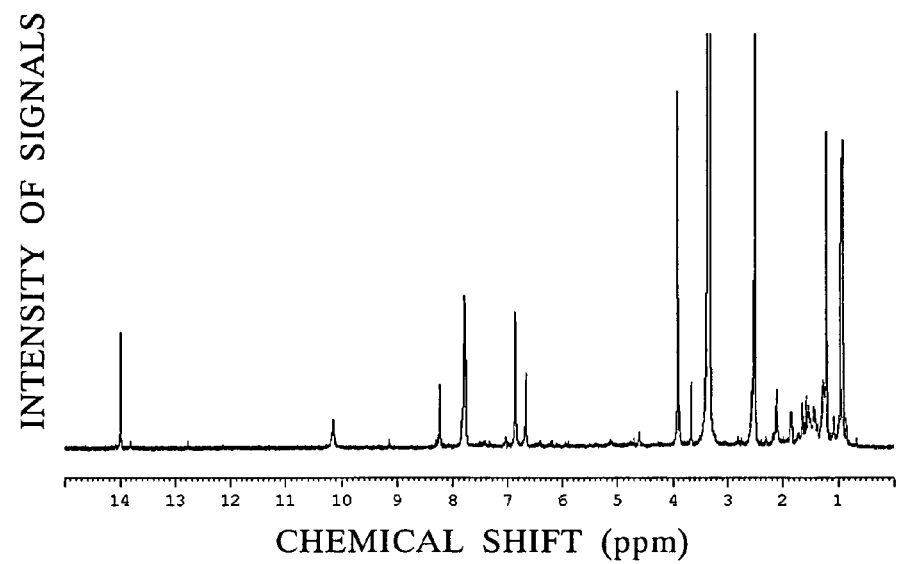
CHEMICAL SHIFT (ppm)
[Figure 10]
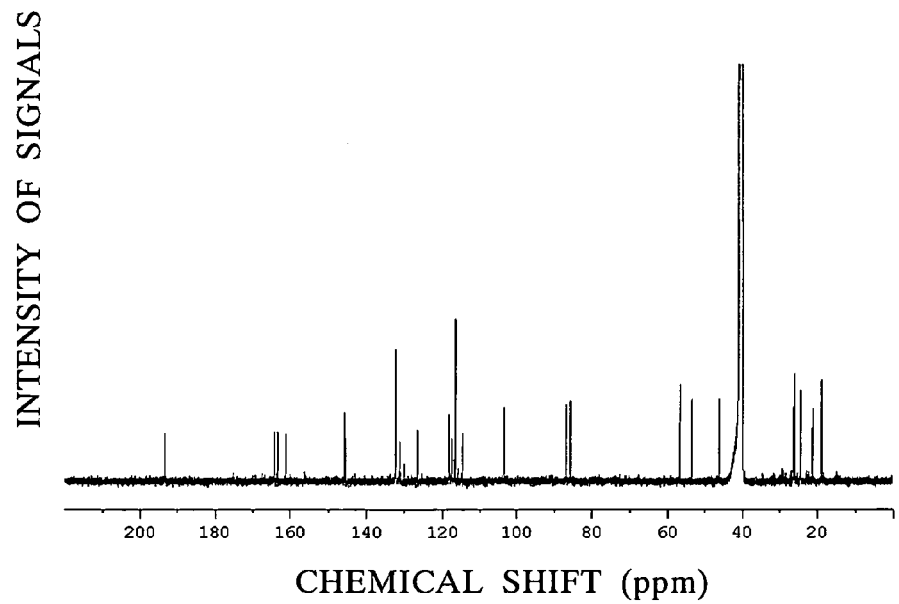
CHEMICAL SHIFT (ppm)

[Figure 11]
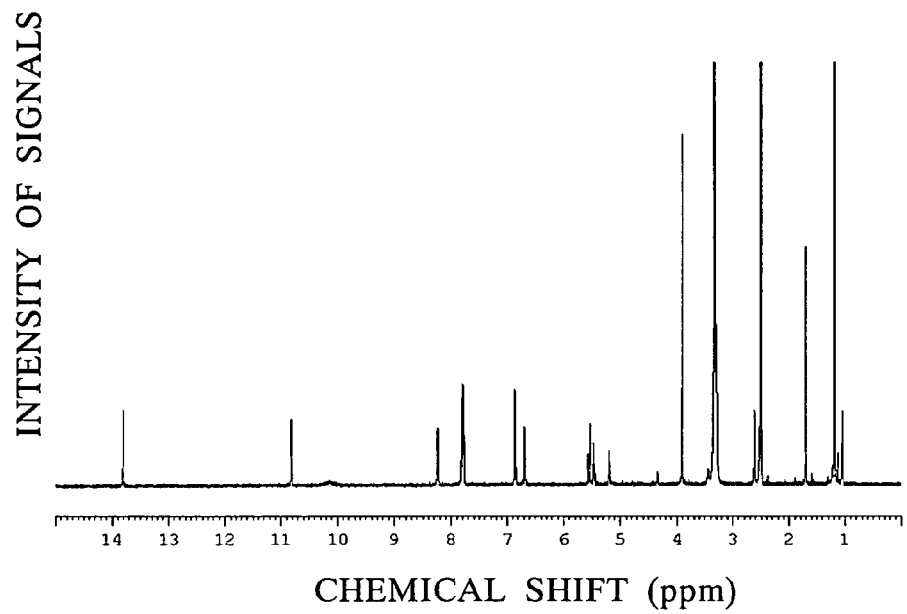
[Figure 12]
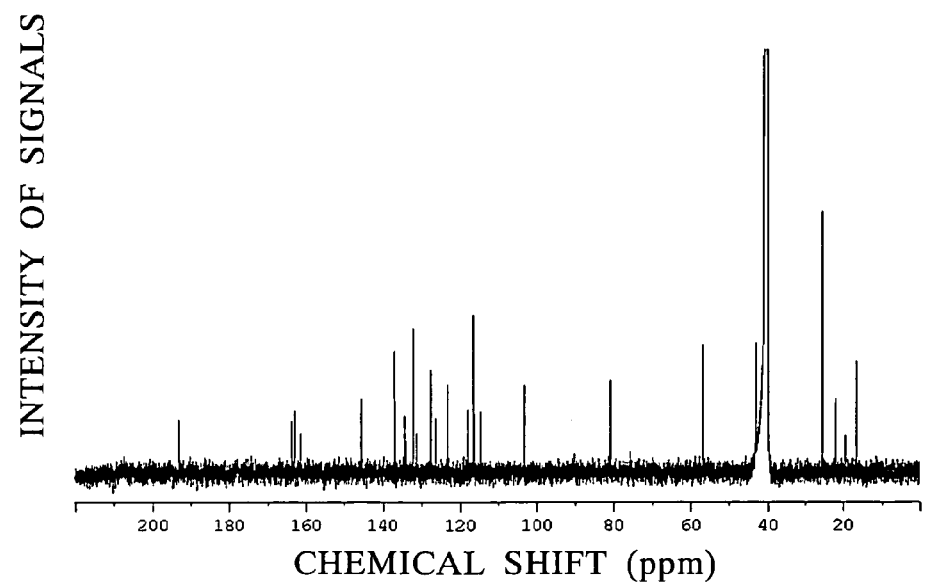

[Figure 13]
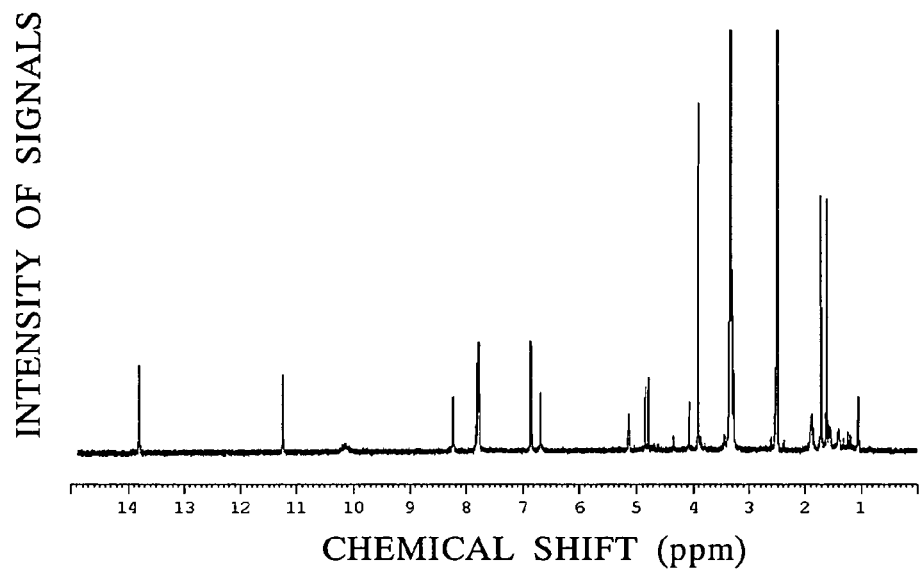
[Figure 14]
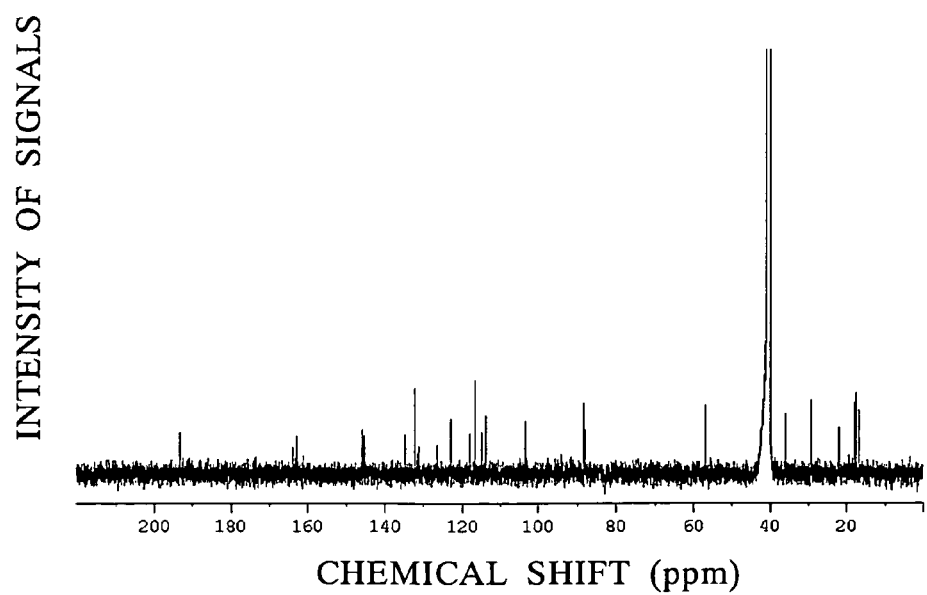

[Figure 15]
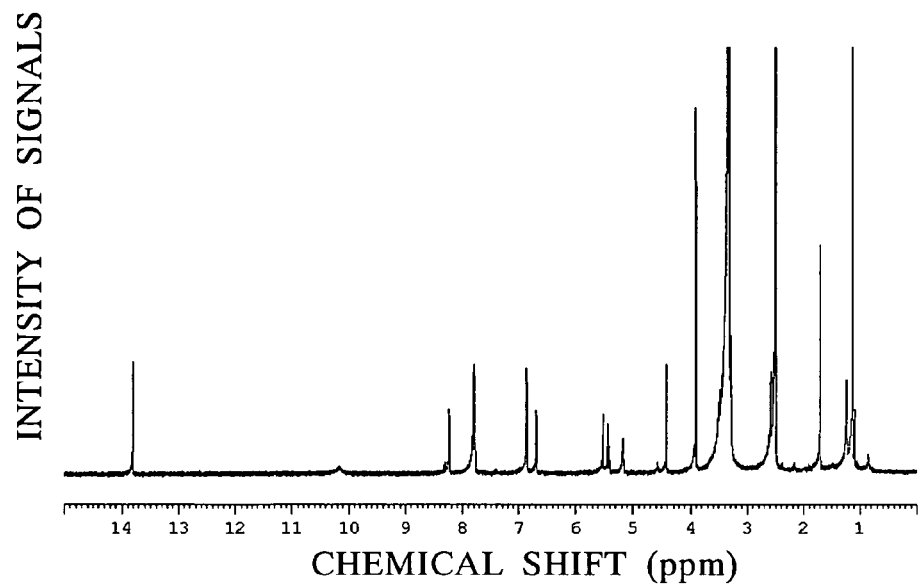
[Figure 16]
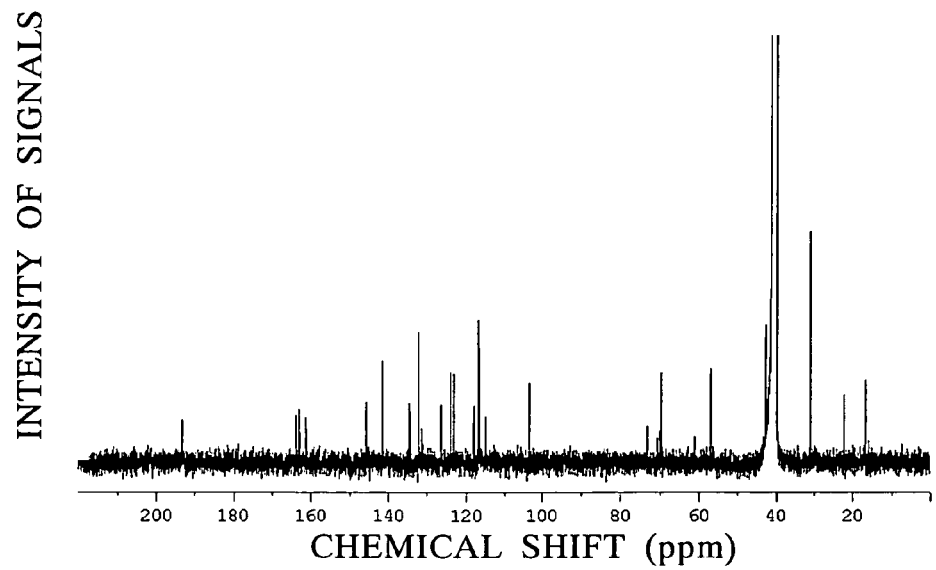

[Figure 17]
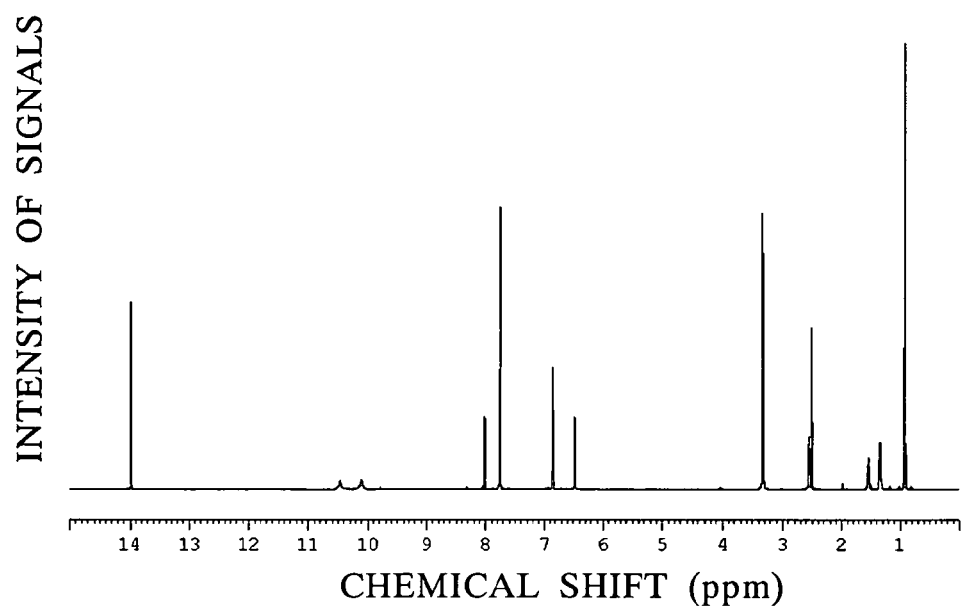

CHALCONE COMPOUNDS

TECHNICAL FIELD

The present invention relates to a novel chalcone compound, and a medicament, foodstuff or the like utilizing the physiological action of the compound.

BACKGROUND ART

Chalcone compounds are a generic term for compounds having a chalcone backbone having the following formula (Ka 1). As these compounds, various compounds obtained by extraction or synthesis from natural products have been known.

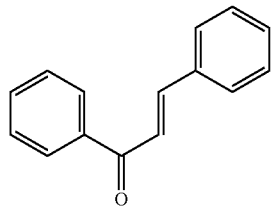

[Ka 1]

In addition, there are a variety of physiological activities of these compounds, depending upon the compounds. For example, cytotoxicity, anticancer activity, chemoprotectant property, anti-mutagenesity, antibacterial activity, antiviral activity, antiprotozoal property, insecticidal action and the like have been known (for example, Non-Patent Publication 1). In addition, the present inventors have found that these chalcone compounds have enhancing actions for nerve growth factor (NGF) production (for example, Patent Publication 1).

Patent Publication 1: WO 01/54682
Non-Patent Publication 1: J. R. Dimmock and three others, *Current Medicinal Chemistry* (*the Netherlands*), 1999, 6, 1125-1149

DISCLOSURE OF THE INVENTION

Problems to be Solved by the Invention

An object of the present invention is to provide a novel chalcone compound, and a medicament, foodstuff or the like utilizing the physiological action of the compound.

Means to Solve the Problems

Summarizing the present invention, a first invention of the present invention relates to a chalcone compound represented by any one of the following formulas (1) to (9):

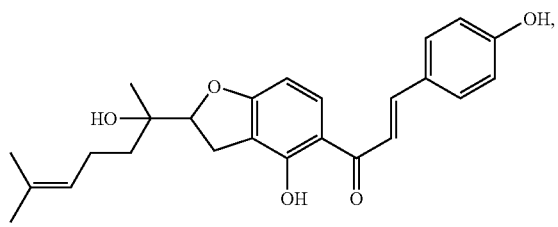

(1)

[Ka 2]

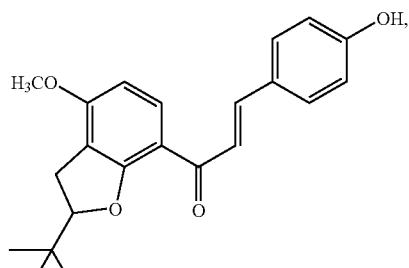

(2)

[Ka 3]

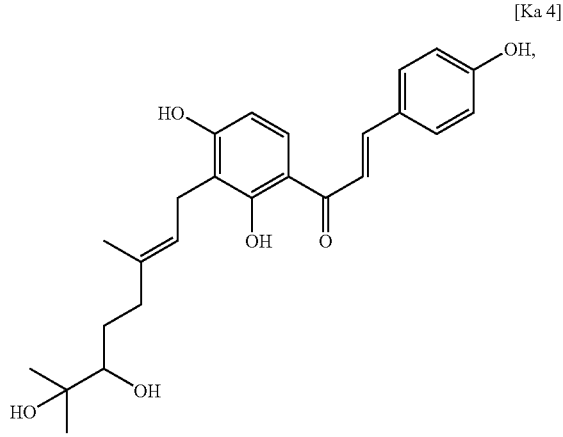

(3)

[Ka 4]

(4)

[Ka 5]

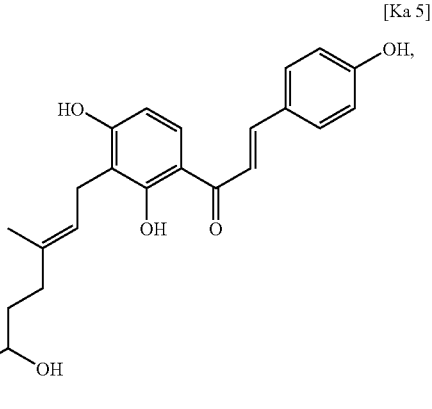

(4)

[Ka 5]

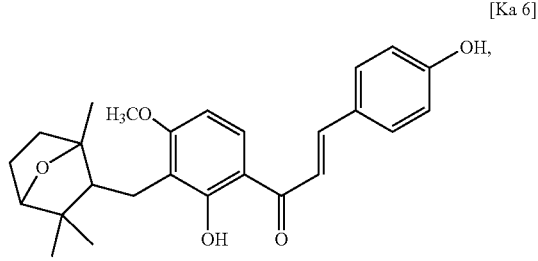

(5)

[Ka 6]

-continued

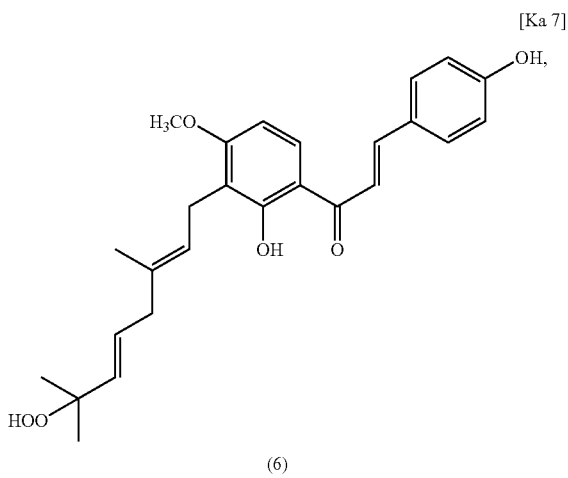

(6)

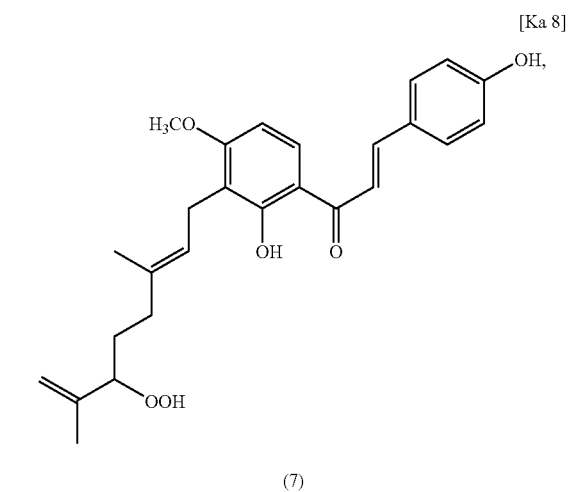

(7)

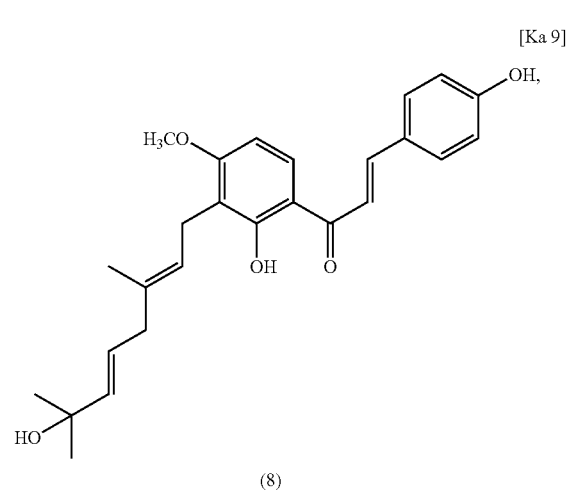

(8)

-continued

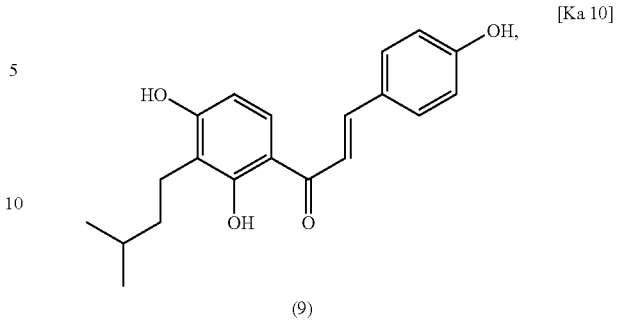

(9)

its derivative, or a salt thereof.

A second invention of the present invention relates to a therapeutic agent or prophylactic agent, characterized in that the agent comprises as an effective ingredient the compound as defined in the first invention of the present invention, its derivative, or a salt thereof, wherein the therapeutic agent or prophylactic agent of a disease shows sensitivity to the compound. In the second invention of the present invention, the disease showing sensitivity to the compound is exemplified by a disease requiring suppression of nitrogen monoxide (NO) production or inhibition of aldose reductase for treatment or prevention thereof.

A third invention of the present invention relates to a suppressive agent of NO production or an inhibitory agent of aldose reductase, characterized in that the agent comprises as an effective ingredient the compound as defined in the first invention of the present invention, its derivative, or a salt thereof.

A fourth invention of the present invention relates to a food, beverage or feed, characterized in that the food, beverage or feed comprises the compound as defined in the first invention of the present invention, its derivative, or a salt thereof. In the fourth invention of the present invention, the food, beverage or feed is useful for treatment or prevention of a disease showing sensitivity to the compound. In addition, in this invention, the disease showing sensitivity to the compound is a disease requiring suppression of NO production or inhibition of aldose reductase.

EFFECTS OF THE INVENTION

According to the present invention, there is provided a novel chalcone compound, its derivative, or a salt thereof. Since the compound has a suppressive action of NO production or an inhibitory action of aldose reductase, the compound is useful as an effective ingredient for a medicament, a food, a beverage or a feed, utilizing the physiological activities. In addition, the medicament or the like provided by the present invention has a therapeutic or prophylactic effect for a disease showing sensitivity to the compound, including, for example, a disease requiring suppression of NO production or inhibition of aldose reductase.

BRIEF DESCRIPTION OF THE DRAWINGS

FIG. 1 A chart showing $^1$H-NMR spectrum of TB3.
FIG. 2 A chart showing $^{13}$C-NMR spectrum of TB3.
FIG. 3 A chart showing $^1$H-NMR spectrum of TB4.
FIG. 4 A chart showing $^{13}$C-NMR spectrum of TB4.
FIG. 5 A chart showing $^1$H-NMR spectrum of TB5.
FIG. 6 A chart showing $^{13}$C-NMR spectrum of TB5.

FIG. 7 A chart showing ¹H-NMR spectrum of TB6.
FIG. 8 A chart showing ¹³C-NMR spectrum of TB6.
FIG. 9 A chart showing ¹H-NMR spectrum of TB7.
FIG. 10 A chart showing ¹³C-NMR spectrum of TB7.
FIG. 11 A chart showing ¹H-NMR spectrum of TB8.
FIG. 12 A chart showing ¹³C-NMR spectrum of TB8.
FIG. 13 A chart showing ¹H-NMR spectrum of TB9.
FIG. 14 A chart showing ¹³C-NMR spectrum of TB9.
FIG. 15 A chart showing ¹H-NMR spectrum of a compound (C081).
FIG. 16 A chart showing ¹³C-NMR spectrum of a compound (C081).
FIG. 17 A chart showing ¹H-NMR spectrum of a compound (C042).

BEST MODE FOR CARRYING OUT THE INVENTION

The present inventors have found a novel compound represented by any one of the above-mentioned formulas (1) to (9), its derivative, or a salt thereof (which may be referred to herein as the compound of the present invention), and the suppressive action of NO production and the inhibitory action of aldose reductase owned by the compound, thereby making it possible to provide a medicament, foodstuff, or a feed, comprising the compound as an effective ingredient. The compound of the present invention, its derivative, or a salt thereof can have the same level of action. The compounds of the above-mentioned formulas (1) to (7) are novel compounds isolated from *Angelica keiskei* koidz. of an edible plant belonging to Umbelliferae.

The compound of the present invention may be a naturally derived product, or a synthetic product or semi-synthetic product. The natural product is preferably those derived from an edible plant, and the edible plant is exemplified by *Angelica keiskei* koidz., which is a plant belonging to Umbelliferae. In addition, when various isomers of the compound of the present invention are present, any of them can be arbitrarily used in the present invention. The compound of the present invention can be used alone or in admixture of two or more kinds.

For example, the compound of the present invention which is derived from a natural product can be prepared by a combination of known preparation methods. For example, as to the preparation of the compound of the present invention from a natural product, the compound can be purified from a substance containing the compound of the present invention, for example, a plant such as *Angelica keiskei* koidz. As the purification means, there may be employed a known purification means such as chemical method or physical method, and conventionally known purification methods such as gel filtration, fractionation method with a molecular weight fractionation membrane, solvent extraction method, and various chromatographic methods using ion exchange resin, silica gel, reverse phase resin, or the like may be combined to purify the compound of the present invention. For example, the compounds of the above-mentioned formulas (1) to (7), which are compounds of the present invention, can be prepared by referring to Examples 1 to 7 set forth below.

The compound of the present invention which is obtained by synthesis can be prepared by combining known preparation methods. The method of synthesis may be, for example, referred to Alessandra Lattanzi et al., *Synlett.* 2002, No. 6, p 942-946; L. Claisen A. et al., *Ber.* 1881, No. 14, p 2460; and the like. For example, the compound represented by the above-mentioned formula (9), which is a compound of the present invention can be obtained by chemical synthesis by referring to Example 9 set forth below.

Also, the compound of the present invention which is obtained by semi-synthesis can be obtained, for example, by subjecting a chalcone compound derived from a natural product as a raw material to organic synthesis. For example, the compound represented by the above-mentioned formula (8), which is a compound of the present invention, can be obtained by subjecting the compound represented by the above-mentioned formula (6) to a reducing treatment by referring to Example 8 set forth below. The method of organic synthesis other than the reducing treatment may be, for example, referred to Alessandra Lattanzi et al., *Synlett.* 2002, No. 6, p 942-946; L. Claisen A. et al., *Ber.* 1881, No. 14, p 2460; and the like.

The derivative of the compound represented by each of the above-mentioned formulas (1) to (9) as used herein refers to a compound prepared by using the compound as an original compound, wherein the compound has the same level of actions as each of the compounds represented by the formulas (1) to (9), i.e., a suppressive action of NO production or an inhibitory action of aldose reductase. The derivative includes, for example, a compound capable of being easily hydrolyzed in a body to exhibit the desired effects (prodrug), such as an ester form, an ether form, or a glycoside form of each of the compounds represented by the above-mentioned formulas (1) to (9). The prodrug may be prepared in accordance with a known method. The derivative may be a salt thereof.

In addition, in the compound of the present invention, as the salt, a pharmacologically acceptable salt is preferable. The salt usable in the present invention is exemplified by, for example, alkali metal salts, alkaline earth metal salts, salts with an organic base and the like. As the salt, a pharmacologically acceptable salt is preferable. Here, the pharmacologically acceptable salt means a salt which is substantially atoxic against an organism. The salts include, for example, salts with sodium, potassium, calcium, magnesium, ammonium or protonated benzathine (N,N'-di-benzylethylenediamine), choline, ethanolamine, diethanolamine, ethylenediamine, meglamine (N-methylglucamine), benethamine (N-benzylphenetylamine), piperazine or tolomethamine (2-amino-2-hydroxymethyl-1,3-propanediol).

According to the present invention, there is provided a therapeutic agent or prophylactic agent of a disease sensitive to the compound of the present invention, wherein the agent comprises the compound as an effective ingredient (which may be referred to herein as the therapeutic agent or the prophylactic agent of the present invention). The disease sensitive to the compound refers to a disease for which therapeutic effects or prophylactic effects can be obtained by the compound. The disease includes, for example, a disease requiring suppression of NO production or inhibition of aldose reductase.

Vascularization is essential for an increase in solid cancer, and vascular endothelial growth factor/vascular permeability-enhancing factor (VEGF) plays a key role in this process. VEGF in various cancerous cells is induced by NO. In other words, the VEGF production is suppressed by suppressing the NO production of the cancerous cells, thereby resulting in inhibition of vascularization in the surrounding of the cancerous cells, whereby cancer can be necrotized.

In addition, NO reacts with an amine under the physiological conditions of a neutral pH to generate a nitrosoamine. This nitrosoamine has been known to show carcinogenicity by damaging DNA. Also, NO production is enhanced in a patient infected with *Clonorchis sinensis* or a patient suffering from cirrhosis, which has immunologically high association with cancer. Therefore, carcinogenesis of a high-risk group can be prevented by suppressing NO production.

NO also induces an edema characteristically found in an inflammatory lesion, in other words, enhancing action for vascular permeability [*Japanese Journal of Cancer Research*, 85, 331-334 (1994)], or enhances biosynthesis of a prostaglandin, which is an inflammatory mediator [*Proceedings of the National Academy of Sciences of the USA*, 90, 7240-7244 (1993)]. On the other hand, NO rapidly reacts with a superoxide radical to generate a peroxynitrite ion, and the peroxynitrite ion is considered to cause an inflammatory cell or a tissue disorder.

In addition, in a synovial fluid of a lesion portion of a patient suffering from arthritis such as chronic rheumatoid arthritis, rheumatic osteoarthritis, gouty arthritis, or Behçet's disease, NO at a high concentration is contained as compared to a synovial fluid of normal articulation of the same patient or an articulation of a normal individual.

Since the compound of the present invention has a suppressive action of NO production as described in Example 11, the compound is useful for the carcinogenetic diseases and the inflammatory diseases mentioned above. The disease requiring suppression of NO production for which the compound of the present invention is effective includes diseases such as carcinogenetic diseases, inflammatory diseases, chronic rheumatic arthritis, rheumatic osteoarthritis, gouty arthritis, and Behçet's disease.

The aldose reductase (hereinafter referred to as AR in some cases) is an enzyme involved in a polyol pathway, which is one of the glucose metabolism pathways in a living body. The pathway comprises a reducing pathway from glucose to sorbitol in which AR is involved, and a dehydrogenation reaction pathway from sorbitol to D-fructose in which sorbitol dehydrogenase (hereinafter referred to as SDH in some cases) is involved. If the amount of glucose allowed to flow into a cell is increased, the glucose which cannot be treated with a glycolytic pathway enhances the polyol pathway. However, since the SDH activity is lower than the AR activity, sorbitol, which is an intermediate metabolite, is produced in a large amount if the glucose is allowed to flow continuously. As to various diseases caused by accumulation of sorbitol as mentioned above, in other words, diseases which are onset as diabetic complications, there have been known, for example, diseases such as cataract, peripheral nerve diseases, nephritic diseases, infections caused by lowering of phagocytotic action of leukocytes, diabetic coma, and arteriosclerosis caused by atheromatous degeneration in the great vessel wall.

Since the compound of the present invention has an inhibitory action for AR as described in Example 10, the compound is useful for the diabetic complications mentioned above. The disease requiring inhibitory action for AR for which the compound of the present invention is effective is exemplified by, for example, diseases such as cataract, peripheral nerve diseases, nephritic diseases, infections caused by lowering of phagocytotic action of leukocytes, diabetic coma, and arteriosclerosis caused by atheromatous degeneration in the great vessel wall. Also, the compound of the present invention can be used together with other therapeutic agents for diabetes.

The therapeutic agent or prophylactic agent of the present invention mentioned above comprises the compound of the present invention as an effective ingredient, and can be manufactured by combining the compound with a known pharmaceutical carrier to form into a preparation. In general, these compounds are formulated with a pharmacologically acceptable liquid or solid carrier, and a solvent, a dispersant, an emulsifier, a buffer, a stabilizer, an excipient, a binder, a disintegrant, a lubricant, or the like is added thereto as desired, so that a solid agent such as a tablet, a granule, a powder, a fine powder, and a capsule, or a liquid agent such as a common liquid agent, a suspension agent or an emulsion agent can be formed. In addition, there can be also made into a dry product which can be made liquid by adding an appropriate carrier before use.

The pharmaceutical carrier can be selected depending upon the administration form and preparation form of the therapeutic agent or prophylactic agent. In the case of an orally administered preparation comprising a solid composition, the preparation can be produced in the form of a tablet, a pill, a capsule, a powder, a fine powder, a granule or the like, and there can be utilized, for example, starch, lactose, saccharose, mannitol, carboxymethyl cellulose, cornstarch, an inorganic salt or the like. In addition, during the preparation of the orally administered preparation, a binder, a disintegrant, a surfactant, a lubricant, a fluidity accelerator, a flavor, a colorant, a perfume, and the like can be further formulated. In the case of forming into a tablet or pill, for example, the tablet or pill may be covered with a sugar-coating made of sucrose, gelatin or hydroxypropyl cellulose, or with a film made of a substance soluble in the stomach or intestine as desired. In the case of an orally administered preparation comprising a liquid composition, the preparation can be prepared in the form of a pharmaceutically acceptable emulsion, solution, suspension, syrup, or the like. In this case, for example, purified water, ethanol or the like is utilized as a carrier. Furthermore, an auxiliary agent such as a wetting agent or a suspending agent, a sweetener, a flavor, an antiseptic, or the like may be added as desired.

On the other hand, in the case of a non-orally administered preparation, the preparation can be prepared by dissolving or suspending the above-mentioned effective ingredient of the present invention in a diluent such as distilled water for injection, physiological saline, an aqueous solution of glucose, vegetable oil for injection, sesame oil, peanut oil, soybean oil, corn oil, propylene glycol or polyethylene glycol, in accordance with a conventional method, and adding a microbicide, a stabilizer, an osmotic regulator, a soothing agent, or the like as desired. It is also possible to produce a solid composition which is dissolved in sterile water or a sterile solvent for injection before use.

In addition, the prophylactic agent or the therapeutic agent of the present invention can be used as an external preparation. The external preparation includes solid, semi-solid or liquid preparations for percutaneous administration or transmucosal (oral or intranasal) administration. The external preparation also includes suppositories and the like. For example, the external preparation may be prepared as liquid preparations including emulsions, suspensions such as lotions, external tinctures, and liquid agents for transmucosal administration; ointments such as oily ointments and hydrophilic ointments; medical adhesives for percutaneous administration or transmucosal administration such as films, tapes and poultices; and the like.

Each of the therapeutic agent or the prophylactic agent in the various forms of preparation as described above can be appropriately produced in accordance with conventional methods by utilizing known pharmaceutical carriers and the like. Also, the content of the effective ingredient in the therapeutic agent or the prophylactic agent is not particularly limited, as long as the content is in an amount so that the effective ingredient can be preferably administered within the dose range described below in consideration of administration form, administration method and the like of the preparation.

The content of the above-mentioned effective ingredient in the therapeutic agent or prophylactic agent of the present invention is not particularly limited. Usually, the content is exemplified by preferably from 0.001 to 80% by weight, more preferably from 0.01 to 50% by weight, especially preferably from 0.1 to 20% by weight.

The dose of the therapeutic agent or prophylactic agent of the present invention is changeable and properly set depending upon its preparation form, administration method, purpose of use, and age, body weight, symptom or the like of a patient to which the agent is applied, or the like. Generally, the dose of the agent, in terms of the dose of the effective ingredient contained in the preparation, is preferably from 10 µg to 1 g/kg body weight, more preferably from 50 µg to 500 mg/kg body weight, even more preferably from 100 µg to 100 mg/kg body weight, for human (for example, adult) per day. As a matter of course, the dose varies depending upon various conditions, so that an amount smaller than the dose mentioned above may be sufficient, or an amount exceeding the dose range may be required. In addition, the administration method of the therapeutic agent or prophylactic agent of the present invention is not particularly limited, and may be appropriately set depending upon purpose of use, and age, symptom or the like of a patient. For example, the administration method includes oral administration, intravenous administration, percutaneous administration, and the like. In the case of oral administration, the therapeutic agent or prophylactic agent of the present invention can be directly orally administered, or the agent can be added to any foodstuff to be taken on a daily basis.

The term "medicament" as used herein conveniently refers not only to the therapeutic agent or prophylactic agent of the present invention described above, but also to the suppressive agent of NO production or the inhibitory agent of aldose reductase of the present invention in some cases, which will be described below.

In addition, the present invention can provide a suppressive agent of NO production or an inhibitory agent of aldose reductase, wherein the agent comprises the compound of the present invention as an effective ingredient. The suppressive agent of NO production or the inhibitory agent of aldose reductase of the present invention may be the above-mentioned effective ingredient itself, or a composition comprising the above-mentioned effective ingredient. In the embodiment of the present invention, the salt as the effective ingredient is preferably a pharmacologically acceptable salt. The suppressive agent of NO production or the inhibitory agent of aldose reductase of the present invention may be prepared by, for example, formulating the above-mentioned effective ingredient with other ingredients which can be used for the same application as the effective ingredient, and forming into a form of reagent usually used according to the above-mentioned process for preparing the therapeutic agent or prophylactic agent. The content of the above-mentioned effective ingredient in the suppressive agent of NO production or the inhibitory agent of aldose reductase of the present invention is not particularly limited, as long as the content is in an amount so that the desired effects of the present invention can be exhibited in consideration of administration method, purpose of use or the like of the agent. Usually, the content of the effective ingredient is exemplified by preferably from 0.001 to 100% by weight, more preferably from 0.01 to 80% by weight, especially preferably from 0.1 to 80% by weight. Also, the amount of the agent used is not particularly limited, as long as the desired effects of the present invention can be exhibited. Especially in the case where the agent is administered to a living body, the agent may be preferably used in an amount so that the effective ingredient can be administered within the dose range of the effective ingredient for the above-mentioned therapeutic agent or prophylactic agent. The administration method is also not particularly limited, and may be appropriately set in the same manner as in the therapeutic agent or prophylactic agent mentioned above. The suppressive agent of NO production or the inhibitory agent of aldose reductase of the present invention is useful in a disease requiring suppression of NO production or inhibition of aldose reductase. In addition, the suppressive agent of NO production or the inhibitory agent of aldose reductase of the present invention is also useful for screening of drugs for these diseases. Furthermore, the suppressive agent of NO production or the inhibitory agent of aldose reductase of the present invention is useful for functional studies relating to physical changes in these diseases.

In addition, according to the present invention, there is provided a food, beverage or feed, comprising the compound of the present invention (which may be referred to herein as the food, beverage or feed of the present invention, or conveniently, which may be referred to as the foodstuff or the like of the present invention). The food, beverage or feed of the present invention is useful as a food, beverage or feed for the treatment or prevention of a disease showing a sensitivity to the compound. Here, the food, beverage or feed of the present invention refers to one encompassing a functional food (designated health food) provided for the purpose of the treatment or prevention of the disease. The disease showing sensitivity to the compound is exemplified by, for example, a disease to which the therapeutic agent or prophylactic agent of the present invention mentioned above is applied. For example, the food, beverage or feed in which the compound of the present invention is contained, added and/or diluted is very useful for amelioration of symptoms or prevention of a disease requiring suppression of NO production or inhibition of aldose reductase by the inhibitory action of NO production or the inhibitory action of aldose reductase of the food, beverage or feed. Therefore, the food or beverage of the present invention is suitably taken for an individual who cares about his/her blood sugar level, an individual who is in pain or feeling something wrong in the limbs or a joint, or an individual who feels lowering in eyesight, swelling of the body, or numbness.

As used herein, the above-mentioned term "containing (ed)" refers to an embodiment of containing the effective ingredient usable in the present invention in the food, beverage or feed; the above-mentioned term "adding(ed)" refers to an embodiment of adding the effective ingredient usable in the present invention to a raw material for the food, beverage or feed; and the above-mentioned term "diluting(ed)" refers to an embodiment of adding a raw material for the food, beverage or feed to the effective ingredient usable in the present invention.

The process for preparing the food, beverage or feed of the present invention is not particularly limited. A generally used process for preparing a food, beverage or feed can be employed, as long as the resulting food, beverage or feed may contain the compound of the present invention as the effective ingredient, preferably exemplified by a food, beverage or feed containing the effective ingredient of the present invention in a high content. The expression "contained . . . in a high content" as used herein means that the weight of the compound of the present invention per unit weight of the food, beverage or feed of the present invention is larger than the weight of the compound of the present invention per unit weight of the raw material, for example, *Angelica keiskei* koidz.

The food or beverage of the present invention is not particularly limited. The food or beverage includes, for example, processed agricultural and forest products, processed stock raising products, processed marine products and the like, including processed grain products, processed fat and oil products, processed soybean products, processed meat products, marine products, milk products, processed vegetable and fruit products, confectioneries, alcohol beverages, luxury drinks, seasonings, canned, binned or pouched foods, semi-dry or concentrated foods, dry foods, frozen foods, solid foods, liquid foods, spices, and the like.

In the food or beverage of the present invention, its shape is not particularly limited, as long as the above-mentioned effective ingredient is contained, added and/or diluted. For example, the shape includes those which can be easily taken orally such as tablets, granules and capsules.

The content of the above-mentioned effective ingredient in the food or beverage of the present invention is not particularly limited, and the content can be appropriately selected from the viewpoints of sensory aspect and exhibition of activity. The content of the effective ingredient is, for example, 0.00001% by weight or more, preferably from 0.0001 to 10% by weight, even more preferably from 0.0006 to 6% by weight, per 100% by weight of the food. The content is, for example, 0.00001% by weight or more, preferably from 0.0001 to 10% by weight, even more preferably from 0.0006 to 6% by weight, per 100% by weight of the beverage. In addition, in the case of the food or beverage containing the effective ingredient of the present invention in a high content, it is preferable that the content of the effective ingredient is, for example, 0.0001% by weight or more, preferably from 0.0005 to 10% by weight, even more preferably from 0.001 to 10% by weight, per 100% by weight of the food, and that the content is, for example, 0.0001% by weight or more, preferably from 0.0005 to 10% by weight, even more preferably from 0.001 to 10% by weight, per 100% by weight of the beverage. Also, it is preferable that the food or beverage of the present invention is taken so that the effective ingredient contained therein may be taken in an amount of from 10 µg to 1 g/kg body weight, preferably from 50 µg to 500 mg/kg body weight, even more preferably from 100 µg to 100 mg/kg body weight, per day for human (for example, adult).

In addition, the present invention provides a feed for an organism, comprising the above-mentioned effective ingredient. In still another embodiment, the present invention also provides a method of feeding an organism, characterized by administering the above-mentioned effective ingredient to the organism. In still yet another embodiment, the present invention provides an organism feeding agent characterized in that the organism feeding agent comprises the above-mentioned effective ingredient. The term "comprise(comprising)" as used herein means contain(containing), add(adding), and/or dilute (diluting) as mentioned above, and contain(containing), add(adding), and/or dilute (diluting) has the meaning as mentioned above.

The organism as used herein is not limited, and includes, for example, culturing or breeding animals, pet animals, and the like. The culturing or breeding animal is exemplified by cattle such as *Equus, Bos, Porcus, Ovis, Capra, Camelus*, and *Lama*; experimental animals such as mice, rats, guinea pigs, and rabbits; poultry such as *Chrysolophus*, ducks, *Meleagris*, and *Struthioniformes*; pisces; crustaceae; or shellfish. The pet animal includes dogs, cats, and the like. The feed is exemplified by a feed for sustenance of and/or amelioration in physical conditioning. The organism feeding agent is exemplified by immersion agents, feed additives, and beverage additives.

According to these inventions, the same effects can be expected to be exhibited as those of the above-mentioned therapeutic agent or prophylactic agent of the present invention, on the basis of the suppressive action of NO production or the inhibitory action of aldose reductase of the above-mentioned effective ingredient usable in the present invention, in the organism exemplified above for applying these. In other words, the feed or the organism feeding agent of the present invention has a therapeutic or prophylactic effect for a disease requiring suppression of NO production or inhibition of aldose reductase in the organism to which the feed or organism feeding agent is applied.

The above-mentioned effective ingredient usable in the present invention is usually administered in an amount of from 10 µg to 1 g/kg body weight, preferably from 50 µg to 500 mg/kg body weight, more preferably from 100 µg to 100 mg/kg body weight to the subject organism, per day. The administration can be made by previously adding and mixing the effective ingredient of the present invention in a raw material for an artificially formulated feed to be given to a subject organism, or mixing the effective ingredient of the present invention with a powder raw material for an artificially formulated feed, and thereafter further adding and mixing the mixture with other raw materials. The content of the above-mentioned effective ingredient in the feed is not particularly limited, and the content can be appropriately set in accordance with its purposes. It is preferable that the content of the effective ingredient is, for example, 0.00001% by weight or more, preferably from 0.0001 to 30% by weight, even more preferably from 0.001 to 15% by weight, per 100% by weight of the feed. In addition, in the case of the feed containing the effective ingredient of the present invention in a high content, it is preferable that the content of the effective ingredient is, for example, 0.0001% by weight or more, preferably from 0.0005 to 30% by weight, even more preferably from 0.001 to 30% by weight, per 100% by weight of the feed.

The process for preparing the feed according to the present invention is not particularly limited, and its composition may be set in accordance with a general feed, as long as the above-mentioned effective ingredient according to the present invention may be contained in the feed prepared. The organism feeding agent may be prepared, used and the like in accordance with the case of the above-mentioned feed.

By allowing a subject organism to take the feed comprising the above-mentioned effective ingredient usable in the present invention having suppressive action of NO production or inhibitory action of aldose reductase, or immersing a subject organism into a solution containing the above-mentioned effective ingredient usable in the present invention having suppressive action of NO production or inhibitory action of aldose reductase, the physical conditions of the cattle, experimental animals, poultry, pet animals or the like can be well sustained or ameliorated. The embodiment illustrated herein is one embodiment of the method of feeding an organism provided by the present invention.

In the present invention, the content of the compound of the present invention in the medicament, foodstuff or feed may be at a level so as to give the desired effects in a living body by its administration, intake or the like. It is preferable that the compound of the present invention is contained in a large amount as compared to that of the corresponding known foodstuff or the like.

No toxicity is found even when the above-mentioned effective ingredient usable in the present invention is administered to an organism in an amount effective for the exhibition of its action. For example, in the case of oral administration, no cases of deaths are found even when each of the compounds represented by the above-mentioned formulas (1) to (9), or their optically active isomers, and salts thereof is administered to a mouse at 1 g/kg body weight in a single dose. In addition, no cases of deaths are found in the oral administration of rats, even when the above-mentioned effective ingredient is orally administered to a rat at 1 g/kg body weight in a single dose.

EXAMPLES

The present invention will be described more concretely hereinbelow by means of the examples, but the present invention is by no means limited to these descriptions. Unless specified otherwise, % in all these examples means % by volume. In the present specification, the compound represented by the formula (1) above is referred to as TB3, the compound represented by the formula (2) above as TB4, the compound represented by the formula (3) above as TB5, the compound represented by the formula (4) above as TB6, the compound represented by the formula (5) above as TB7, the compound represented by the formula (6) above as TB8, the compound represented by the formula (7) above as TB9, the compound represented by the formula (8) above as compound (C081), and the compound represented by the formula (9) above as compound (C042), in some cases.

Example 1

Preparation of TB3

(1) Fifteen liters of ethanol was added to 5 kg of a dry powder of root portions of *Angelica keiskei* koidz., and extracted at room temperature for 30 minutes. After suction filtration, the ethanol extract and the residue were separated. The same procedures were repeated twice for the residue. Thereafter, the ethanol extracts were combined, and the combined extract was concentrated under reduced pressure, to give a concentrate of an ethanol extract.

(2) The concentrate of the ethanol extract obtained in item (1) of Example 1 was dissolved in 2 L of a 25% aqueous ethanol solution, and thereafter fractionated by using reverse phase chromatography. As the resin, Cosmosil 140 C18-OPN (manufactured by Nakalai Tesque, Inc.: 400 mL) was used. The elution was carried out with 1 L of a 30% aqueous ethanol solution, 5 L of a 40% aqueous ethanol solution, 4 L of a 75% aqueous ethanol solution, and 3 L of a 100% aqueous ethanol solution in that order.

(3) The fraction eluted with the 75% aqueous ethanol solution obtained in item (2) of Example 1 was concentrated under reduced pressure, and adsorbed on a silica gel (BW-300SP: manufactured by Fuji Silysia Chemical Ltd.: 350 mL). The elution was carried out stepwise with chloroform:hexane at a solvent ratio of 2:1 (800 mL), 10:4 (1800 mL), and ethyl acetate (1400 mL) in that order. The eluates were fractionated 200 mL each for the fractions 1 to 5, 150 mL for the fraction 6, 100 mL each for the fractions 7 to 10, 200 mL each for the fractions 11 to 16, and 1000 mL for the fraction 17 in that order.

(4) The fraction number 17 obtained in item (3) of Example 1 was concentrated under reduced pressure, and adsorbed on a silica gel (350 mL). The elution was carried out stepwise with chloroform:hexane at a solvent ratio of 10:3 (1000 mL), 10:1 (2100 mL), 20:1 (1000 mL), and ethyl acetate (500 mL) in that order. After the initial 2300 mL was eluted, the eluates were fractionated for every 100 mL.

(5) The fraction numbers 23 and 24 obtained in item (4) of Example 1 were concentrated under reduced pressure. Thereafter, the concentrate was dissolved in chloroform, and the recrystallization was carried out with hexane, to give a yellow substance.

(6) The structure of the yellow substance obtained in item (5) of Example 1 was analyzed by measuring various kinds of nuclear magnetic resonance (NMR) spectra with a NMR spectrometer (Model AVANCE 600: manufactured by Bruker BIOSPIN). The signals of NMR are shown below. In addition, the numbers of the peaks are shown in the following formula (Ka 11).

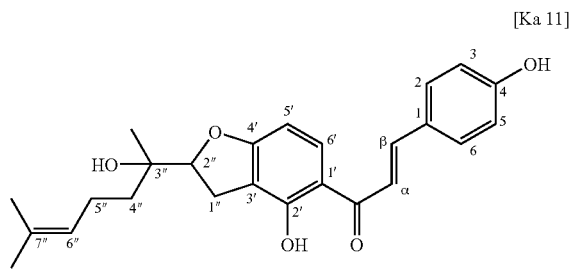

[Ka 11]

$^1$H-NMR (deuterated chloroform): δ1.34 (3H, s, CH$_3$-3"), 1.57 (2H, m, H-4"), 1.65 (3H, s, CH$_3$-7"), 1.71 (3H, s, CH$_3$-7"), 1.79 (1H, s, OH-3"), 2.11 (1H, m, H-5"), 2.19 (1H, m, H-5"), 3.19 (2H, d, J=8.7 Hz, H-1"), 4.82 (1H, t, J=8.7 Hz, H-2"), 5.15 (1H, t, J=6.7 Hz, H-6"), 5.21 (1H, s, OH-4), 6.44 (1H, d, J=8.4 Hz, H-5'), 6.89 (2H, d, J=7.2 Hz, H-3 and H-5), 7.46 (1H, d, J=15.0 Hz, H-α), 7.58 (2H, d, J=7.2 Hz, H-2 and H-6), 7.80 (1H, d, J=8.4 Hz, H-6'), 7.84 (1H, d, J=15.0 Hz, H-β), 13.51 (1H, s, OH-2')

FIG. 1 shows $^1$H-NMR spectrum.

$^{13}$C-NMR (deuterated chloroform): δ18.1 (CH$_3$-7"), 22.4 (C-5"), 23.2 (CH$_3$-3"), 26.1 (CH$_3$-7"), 27.3 (C-1"), 37.1 (C-4"), 74.2 (C-3"), 91.6 (C-2"), 102.1 (C-5'), 114.2 (C-3'), 115.4 (C-1'), 116.4 (C-3 and C-5), 118.6 (C-α), 124.4 (C-6"), 128.2 (C-1), 130.9 (C-2 and C-6), 132.1 (C-6'), 132.7 (C-7"), 144.3 (C-β), 158.3 (C-4), 161.9 (C-2'), 167.0 (C-4'), 192.5 (C=O)

FIG. 2 shows $^{13}$C-NMR spectrum.

Next, the mass spectrum (MS) of the yellow substance obtained in item (5) of Example 1 was measured with a mass spectrometer (DX302: manufactured by JEOL LTD.) by FAB-MS technique.

FAB-MS: m/z 407 (M-H)$^-$: Metanitrobenzyl alcohol was used as the matrix.

From the above results of the NMR spectrum analysis and mass spectrum analysis, the yellow substance obtained in item (5) of Example 1 was identified to be 1-[2,3-dihydro-4-hydroxy-2-(1-hydroxy-1,5-dimethyl-4-hexenyl)-benzofuran-5-yl]-3-(4-hydroxyphenyl)-2-propen-1-one (molecular weight: 408, TB3).

Example 2

Preparation of TB4

(1) The fraction eluted with the 40% aqueous ethanol solution obtained in item (2) of Example 1 was concentrated under reduced pressure, and adsorbed on a silica gel (350 mL). The elution was carried out stepwise with chloroform:methanol at a solvent ratio of 50:1 (960 mL), 40:1 (520 mL), 20:1 (1000 mL), 10:1 (840 mL) and 5:1 (520 mL) in that order. The eluates were fractionated for every 8 mL.

(2) The silica fraction numbers 118 to 132 obtained in item (1) of Example 2 were collected and concentrated to dryness, to give a yellow substance.

(3) The NMR spectra and the mass spectrum of the yellow substance obtained in item (2) of Example 2 were determined in the same manner as in item (6) of Example 1. The signals of NMR are shown below. In addition, the numbers of the peaks are shown in the following formula (Ka 12).

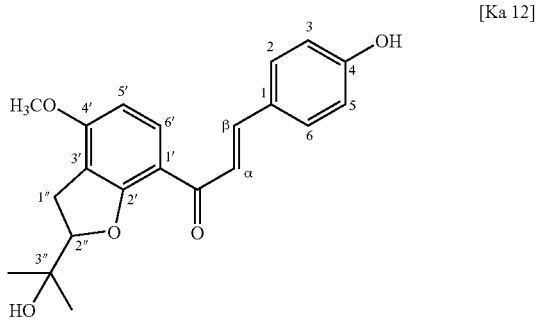

[Ka 12]

$^1$H-NMR (deuterated dimethyl sulfoxide): δ1.18 (3H, s, CH$_3$-3"), 1.28 (3H, s, CH$_3$-3"), 3.07 (2H, m, H-1"), 3.87 (3H, s, OCH$_3$-4'), 4.72 (1H, s, OH-3"), 4.78 (1H, t, J=8.7 Hz, H-2"), 6.65 (1H, d, J=9.0 Hz, H-5'), 6.82 (2H, d, J=8.4 Hz, H-3 and H-5), 7.57 (2H, d, J=8.4 Hz, H-2 and H-6), 7.59 (1H, d, J=15.6 Hz, H-β), 7.69 (1H, d, J=9.0 Hz, H-6'), 7.81 (1H, d, J=15.6 Hz, H-α), 10.02 (1H, s, OH-4)

FIG. 3 shows $^1$H-NMR spectrum.

$^{13}$C-NMR (deuterated dimethyl sulfoxide): δ26.2 (CH$_3$-3"), 26.8 (CH$_3$-3"), 27.6 (C-1"), 56.5 (OCH$_3$-4'), 70.9 (C-3"), 91.5 (C-2"), 105.2 (C-5'), 115.7 (C-3'), 116.0 (C-1'), 116.7 (C-3 and C-5), 123.8 (C-α), 127.0 (C-1), 131.0 (C-2 and C-6), 131.3 (C-6'), 142.7 (C-β), 160.5 (C-4'), 160.6 (C-4), 161.8 (C-2'), 186.5 (C=O)

FIG. 4 shows $^{13}$C-NMR spectrum.

FAB-MS: m/z 353(M-H)$^-$: Metanitrobenzyl alcohol was used as the matrix.

From the above results of the NMR spectrum analysis and mass spectrum analysis, the yellow substance obtained in item (2) of Example 2 was identified to be 1-[2,3-dihydro-2-(1-hydroxy-1-methylethyl)-4-methoxybenzofuran-7-yl]-3-(4-hydroxyphenyl)-2-propen-1-one (molecular weight: 354, TB4).

Example 3

Preparation of TB5

(1) The silica fraction numbers 335 to 349 obtained in item (1) of Example 2 were collected and concentrated under reduced pressure, and thereafter fractionated by using reverse phase chromatography. As the resin, Cosmosil 140 C18-OPN (30 mL) was used. The elution was carried out with 200 mL each of a 10% aqueous ethanol solution, a 15% aqueous ethanol solution, a 20% aqueous ethanol solution, a 25% aqueous ethanol solution, and a 30% aqueous ethanol solution, 500 mL of a 35% aqueous ethanol solution, and 200 mL of a 75% aqueous ethanol solution in that order, and the eluates were fractionated for every 100 mL.

(2) The fraction numbers 6 and 7 obtained in item (1) of Example 3 were collected and concentrated to dryness, to give a yellow substance.

(3) The NMR spectra and the mass spectrum of the yellow substance obtained in item (2) of Example 3 were determined in the same manner as in item (6) of Example 1. The signals of NMR are shown below. In addition, the numbers of the peaks are shown in the following formula (Ka 13).

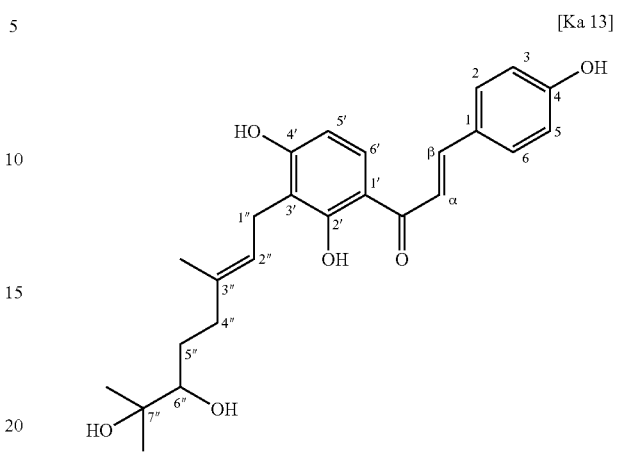

[Ka 13]

$^1$H-NMR (deuterated dimethyl sulfoxide): δ0.96 (3H, s, CH$_3$-7"), 1.02 (3H, s, CH$_3$-7"), 1.16 (1H, m, H-5"), 1.61 (1H, m, H-5"), 1.73 (3H, s, CH$_3$-3"), 1.85 (1H, m, H-4"), 2.15 (1H, m, H-4"), 3.01 (1H, m, H-6"), 3.24 (1H, m, H-1"), 3.31 (1H, m, H-1"), 4.00 (1H, s, OH-7"), 4.23 (1H, d, J=6.0 Hz, OH-6"), 5.19 (1H, t, J=7.2 Hz, H-2"), 6.47 (1H, d, J=8.4 Hz, H—5'), 6.84 (2H, d, J=8.4 Hz, H-3 and H-5), 7.75 (1H, d, J=5.4 Hz, H-α), 7.75 (1H, d, J=5.4 Hz, H-β), 7.75 (2H, d, J=8.4 Hz, H-2 and H-6), 8.03 (1H, d, J=8.4 Hz, H-6'), 10.11 (1H, s, OH-4), 10.55 (1H, s, OH-4'), 14.00 (1H, s, OH-2')

FIG. 5 shows $^1$H-NMR spectrum.

$^{13}$C-NMR (deuterated dimethyl sulfoxide): δ17.0 (CH$_3$-3"), 22.1 (C-1"), 25.4 (CH$_3$-7"), 27.2 (CH$_3$-7"), 30.3 (C-5"), 37.5 (C-4"), 72.4 (C-7"), 78.0 (C-6"), 108.2 (C-5'), 113.6 (C-1'), 115.4 (C-3'), 116.7 (C-3 and C-5), 118.3 (C-α), 122.4 (C-2"), 126.7 (C-1), 130.7 (C-6'), 132.0 (C-2 and C-6), 135.7 (C-3"), 145.0 (C-β), 161.1 (C-4), 163.2 (C-4'), 164.4 (C-2'), 192.6 (C=O)

FIG. 6 shows $^{13}$C-NMR spectrum.

FAB-MS: m/z 425(M-H)$^-$: Metanitrobenzyl alcohol was used as the matrix.

From the above results of the NMR spectrum analysis and mass spectrum analysis, the yellow substance obtained in item (2) of Example 3 was identified to be 1-[2,4-dihydroxy-3-(6,7-dihydroxy-3,7-dimethyl-2-octenyl)phenyl]-3-(4-hydroxyphenyl)-2-propen-1-one (molecular weight: 426, TB5).

Example 4

Preparation of TB6

(1) The silica fraction numbers 142 to 164 obtained in item (1) of Example 2 were collected and concentrated to dryness, and thereafter, the concentrate was dissolved in ethyl acetate. Subsequently, the recrystallization with hexane was carried out, and the formed precipitates and supernatant were separated.

(2) The concentrate of the supernatant obtained in item (1) of Example 4 was adsorbed on a silica gel (100 mL). The elution was carried out with a solvent of hexane:ethyl acetate=7:5, and the eluates were fractionated for every 8 mL.

(3) The silica fraction numbers 41 to 51 obtained in item (2) of Example 4 were collected and concentrated to dryness, to give a yellow substance.

(4) The NMR spectra and the mass spectrum of the yellow substance obtained in item (3) of Example 4 were determined in the same manner as in item (6) of Example 1. The signals of NMR are shown below. In addition, the numbers of the peaks are shown in the following formula (Ka 14).

[Ka 14]

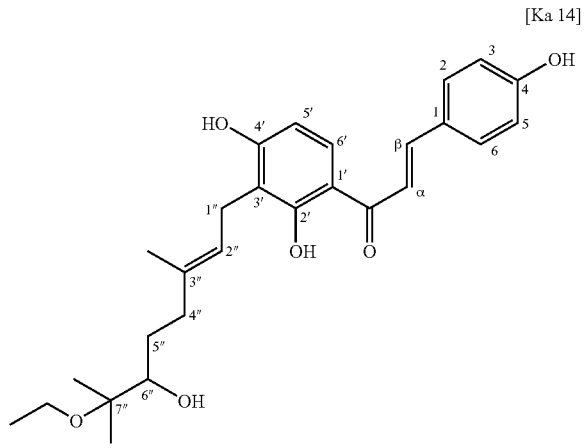

$^1$H-NMR (deuterated dimethyl sulfoxide): δ0.96 (3H, s, CH$_3$-7"), 0.99 (3H, t, J=6.9 Hz, —O—CH$_2$—CH$_3$), 1.04 (3H, s, CH$_3$-7"), 1.15 (1H, m, H-5"), 1.60 (1H, m, H-5"), 1.72 (3H, s, CH$_3$-3"), 1.89 (1H, m, H-4"), 2.13 (1H, m, H-4"), 3.18 (1H, m, H-6"), 3.24 (2H, m, H-1"), 3.29 (2H, m, —O—CH$_2$—CH$_3$), 4.27 (1H, d, J=6.0 Hz, OH-6"), 5.20 (1H, t, J=6.9 Hz, H-2"), 6.47 (1H, d, J=9.0 Hz, H-5'), 6.84 (2H, d, J=8.4 Hz, H-3 and H-5), 7.75 (1H, d, J=4.8 Hz, H-α), 7.75 (1H, d, J=4.8 Hz, H-β), 7.75 (2H, d, J=8.4 Hz, H-2 and H-6), 8.31 (1H, d, J=9.0 Hz, H-6'), 10.11 (1H, s, OH-4), 10.55 (1H, s, OH-4'), 14.00 (1H, s, OH-2')

FIG. 7 shows $^1$H-NMR spectrum.

$^{13}$C-NMR (deuterated dimethyl sulfoxide): δ17.0 (CH$_3$-3"), 17.0 (—O—CH$_2$—CH$_3$), 21.1 (CH$_3$-7"), 22.1 (C-1"), 23.3 (CH$_3$-7"), 29.9 (C-5"), 37.2 (C-4"), 56.6 (—O—CH$_2$—CH$_3$), 75.1 (C-6"), 77.5 (C-7"), 108.2 (C-5'), 113.6 (C-1'), 115.4 (C-3'), 116.7 (C-3 and C-5), 118.3 (C-α), 122.7 (C-2"), 126.7 (C-1), 130.6 (C-6'), 132.0 (C-2 and C-6), 135.5 (C-3"), 145.0 (C-β), 161.1 (C-4), 163.1 (C-4'), 164.4 (C-2'), 192.6 (C=O)

FIG. 8 shows $^{13}$C-NMR spectrum.

FAB-MS: m/z 453(M-H)$^-$: Metanitrobenzyl alcohol was used as the matrix.

From the above results of the NMR spectrum analysis and mass spectrum analysis, the yellow substance obtained in item (3) of Example 4 was identified to be 1-[3-(7-ethoxy-6-hydroxy-3,7-dimethyl-2-octenyl)-2,4-dihydroxyphenyl]-3-(4-hydroxyphenyl)-2-propen-1-one (molecular weight: 454, TB6).

Example 5

Preparation of TB7

(1) The fraction numbers 4 to 22 obtained in item (4) of Example 1 were concentrated under reduced pressure, and thereafter, the concentrate was dissolved in chloroform. Subsequently, the recrystallization with hexane was carried out, and the formed precipitates and supernatant were separated.

(2) The concentrate of the supernatant obtained in item (1) of Example 5 was adsorbed on a silica gel (350 mL). The elution was carried out stepwise with chloroform:hexane at a solvent ratio of 100:1 (1500 mL), 50:1 (2600 mL), 20:1 (2600 mL), and ethyl acetate (300 mL) in that order, and the eluates were fractionated for every 8 mL.

(3) The fractions 21 to 30 obtained in item (2) of Example 5 were collected and concentrated to dryness, to give a yellow substance.

(4) The NMR spectra and the mass spectrum of the yellow substance obtained in item (3) of Example 5 were determined in the same manner as in item (6) of Example 1. The signals of NMR are shown below. In addition, the numbers of the peaks are shown in the following formula (Ka 15).

[Ka 15]

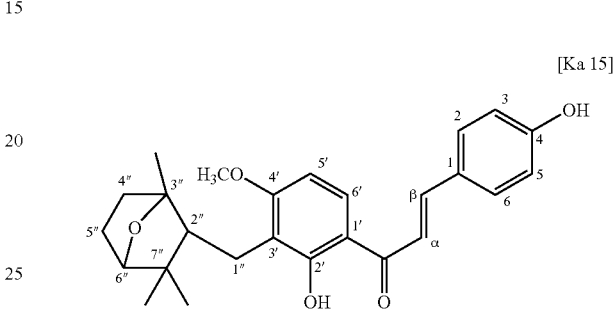

$^1$H-NMR (deuterated dimethyl sulfoxide): δ0.91 (3H, s, CH$_3$-7"), 0.96 (3H, s, CH$_3$-7"), 1.21 (3H, s, CH$_3$-3"), 1.26 (1H, m, H-4"), 1.43 (1H, m, H-4"), 1.53 (1H, m, H-5"), 1.85 (1H, m, H-5"), 2.12 (1H, t, J=7.2 Hz, H-2"), 2.52 (1H, m, H-1"), 2.56 (1H, m, H-1"), 3.62 (1H, d, J=5.4 Hz, H-6"), 3.91 (3H, s, OCH$_3$-4'), 6.67 (1H, d, J=9.0 Hz, H-5'), 6.85 (2H, d, J=8.4 Hz, H-3 and H-5), 7.78 (1H, d, J=15.6 Hz, H-β), 7.78 (2H, d, J=8.4 Hz, H-2 and H-6), 7.83 (1H, d, J=15.6 Hz, H-α), 8.23 (1H, d, J=9.0 Hz, H-6'), 10.15 (1H, s, OH-4), 13.99 (1H, s, OH-2')

FIG. 9 shows $^1$H-NMR spectrum.

$^{13}$C-NMR (deuterated dimethyl sulfoxide): δ19.0 (CH$_3$-3"), 21.3 (C-1"), 24.5 (CH$_3$-7"), 26.0 (CH$_3$-7"), 26.4 (C-5"), 39.9 (C-4"), 46.3 (C-7"), 53.5 (C-2"), 56.8 (OCH$_3$-4'), 85.8 (C-6"), 86.9 (C-3"), 103.7 (C-5'), 114.8 (C-1'), 116.7 (C-3 and C-5), 117.4 (C-3'), 118.2 (C-α), 126.6 (C-1), 131.3 (C-6'), 132.2 (C-2 and C-6), 145.7 (C-β), 161.3 (C-4), 163.5 (C-2'), 164.1 (C-4'), 193.4 (C=O)

FIG. 10 shows $^{13}$C-NMR spectrum.

FAB-MS: m/z 421(M-H)$^-$: Metanitrobenzyl alcohol was used as the matrix.

From the above results of the NMR spectrum analysis and mass spectrum analysis, the yellow substance obtained in item (3) of Example 5 was identified to be 1-[3-(2,5-epoxy-2,6,6-trimethyl-cyclohexylmethyl)-2-hydroxy-4-methoxyphenyl]-3-(4-hydroxyphenyl)-2-propen-1-one (molecular weight: 422, TB7).

Example 6

Preparation of TB8

(1) The silica fraction numbers 10 to 15 obtained in item (3) of Example 1 were collected and concentrated under reduced pressure, and thereafter the concentrate was dissolved in chloroform. Subsequently, the recrystallization with hexane was carried out, and the formed precipitates and supernatant were separated.

(2) The supernatant obtained in item (1) of Example 6 was concentrated under reduced pressure, and thereafter fractionated using reverse phase chromatography. As the column, TSK gel ODS-80Ts (21.5 mm×30 cm: manufactured by Tosoh Corporation) was used. The solvent was distilled water:acetonitrile=15:85, the elution rate was 5 mL/minute, and the detection was carried out at 215 nm. The eluates were fractionated using ultraviolet absorption of the eluates as an index.

(3) The reverse phase chromatography fraction 2 (the fraction containing a detection peak at a retention time of 57.6 minutes) obtained in item (2) of Example 6 were concentrated to dryness, to give a yellow substance.

(4) The NMR spectra and the mass spectrum of the yellow substance obtained in item (3) of Example 6 were determined in the same manner as in item (6) of Example 1. The signals of NMR are shown below. In addition, the numbers of the peaks are shown in the following formula (Ka 16).

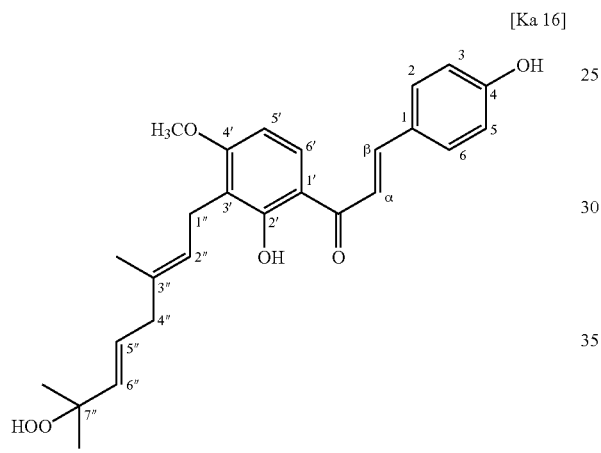

[Ka 16]

$^1$H-NMR (deuterated dimethyl sulfoxide): δ1.19 (3H, s, $CH_3$-7"), 1.19 (3H, s, $CH_3$-7"), 1.70 (3H, s, $CH_3$-3"), 2.62 (2H, d, J=6.6 Hz, H-4"), 3.29 (1H, m, H-1"), 3.31 (1H, m, H-1"), 3.91 (3H, s, $OCH_3$-4'), 5.19 (1H, t, J=6.9 Hz, H-2"), 5.47 (1H, m, H-5"), 5.55 (1H, d, J=15.6 Hz, H-6"), 6.68 (1H, d, J=9.0 Hz, H-5'), 6.85 (2H, d, J=8.4 Hz, H-3 and H-5), 7.78 (2H, d, J=8.4 Hz, H-2 and H-6), 7.79 (1H d, J=13.2 Hz, H-β), 7.83 (1H, d, J=13.2 Hz, H-α), 8.23 (1H, d, J=9.0 Hz, H-6'), 10.14 (1H, s, OH-4), 10.81 (1H, s, OOH-7"), 13.81 (1H, s, OH-2')

FIG. 11 shows $^1$H-NMR spectrum.

$^{13}$C-NMR (deuterated dimethyl sulfoxide): δ16.8 ($CH_3$-3"), 22.1 (C-1"), 25.5 ($CH_3$-7"), 25.5 ($CH_3$-7"), 43.0 (C-4"), 56.9 ($OCH_3$-4'), 81.1 (C-7"), 103.7 (C-5'), 114.9 (C-1'), 116.6 (C-3'), 116.7 (C-3 and C-5), 118.1 (C-α), 123.5 (C-2"), 126.5 (C-1), 127.9 (C-5"), 131.4 (C-6'), 132.3 (C-2 and C-6), 134.3 (C-3"), 137.0 (C-6"), 145.7 (C-β), 161.3 (C-4), 163.0 (C-2'), 163.9 (C-4'), 193.3 (C=O)

FIG. 12 shows $^{13}$C-NMR spectrum.

FAB-MS: m/z 437(M-H)$^-$: Metanitrobenzyl alcohol was used as the matrix.

From the above results of the NMR spectrum analysis and mass spectrum analysis, the yellow substance obtained in item (3) of Example 6 was identified to be 1-[2-hydroxy-3-(7-hydroperoxy-3,7-dimethyl-2,5-octadienyl)-4-methoxyphenyl]-3-(4-hydroxyphenyl)-2-propen-1-one (molecular weight: 438, TB8).

Example 7

Preparation of TB9

(1) The reverse phase chromatography fraction 3 (the fraction containing a detection peak at a retention time of 61.2 minutes) obtained in item (2) of Example 6 was concentrated to dryness, to give a yellow substance.

(2) The NMR spectra and the mass spectrum of the yellow substance obtained in item (1) of Example 7 were determined in the same manner as in item (6) of Example 1. The signals of NMR are shown below. In addition, the numbers of the peaks are shown in the following formula (Ka 17).

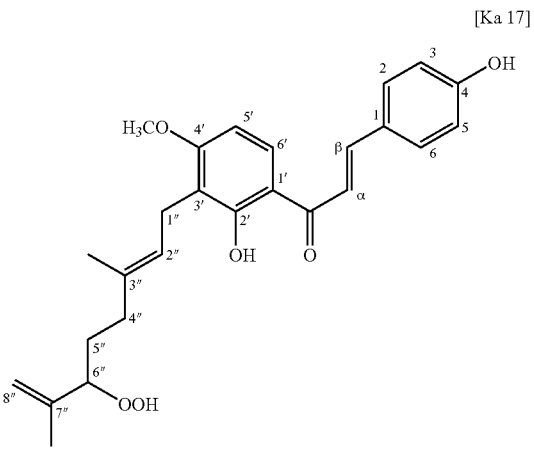

[Ka 17]

$^1$H-NMR (deuterated dimethyl sulfoxide): δ1.40 (1H, m, H-5"), 1.56 (1H, m, H-5"), 1.62 (3H, s, $CH_3$-7"), 1.72 (3H, s, $CH_3$-3"), 1.89 (2H, m, H-4"), 3.27 (1H, m, H-1"), 3.31 (1H, m, H-1"), 3.91 (3H, s, $OCH_3$-4'), 4.07 (1H, t, J=6.9 Hz, H-6"), 4.79 (1H, s, H-8"), 4.84 (1H, s, H-8"), 5.14 (1H, t, J=6.6 Hz, H-2"), 6.68 (1H, d, J=9.0 Hz, H-5'), 6.85 (2H, d, J=8.4 Hz, H-3 and H-5), 7.78 (2H, d, J=8.4 Hz, H-2 and H-6), 7.78 (1H, d, J=15.0 Hz, H-β), 7.83 (1H, d, J=15.0 Hz, H-α), 8.24 (1H, d, J=9.0 Hz, H-6'), 10.15 (1H, s, OH-4), 11.25 (1H, s, OOH-6"), 13.81 (1H, s, OH-2')

FIG. 13 shows $^1$H-NMR spectrum.

$^{13}$C-NMR (deuterated dimethyl sulfoxide): δ16.7 ($CH_3$-3"), 17.7 ($CH_3$-7"), 22.0 (C-1"), 29.5 (C-5"), 36.0 (C-4"), 56.9 ($OCH_3$-4'), 88.2 (C-6"), 103.6 (C-5'), 114.0 (C-8"), 114.9 (C-1'), 116.7 (C-3'), 116.7 (C-3 and C-5), 118.1 (C-α), 122.9 (C-2"), 126.5 (C-1), 131.3 (C-6'), 132.3 (C-2 and C-6), 134.9 (C-3"), 145.3 (C-7"), 145.7 (C-β), 161.3 (C-4), 163.0 (C-2'), 163.8 (C-4'), 193.3 (C=O)

FIG. 14 shows $^{13}$C-NMR spectrum.

FAB-MS: m/z 437(M-H)$^-$: Metanitrobenzyl alcohol was used as the matrix.

From the above results of the NMR spectrum analysis and mass spectrum analysis, the yellow substance obtained in item (1) of Example 7 was identified to be 1-[2-hydroxy-3-

(6-hydroperoxy-3,7-dimethyl-2,7-octadienyl)-4-methoxyphenyl]-3-(4-hydroxyphenyl)-2-propen-1-one (molecular weight: 438, TB9).

Example 8

Preparation of Compound (C081)

(1) One-hundred milligrams of TB8 obtained in item (3) of Example 6 was dissolved in 50 mL of methanol, and triphenylphosphine (manufactured by Tokyo Kasei Kogyo Co., Ltd.: 60 mg) was added to the solution, and the mixture was reacted at room temperature for 1 hour. The reaction mixture was concentrated under reduced pressure, and the concentrate was subjected to thin layer chromatography using chloroform:methanol=10:1 as a developing solvent. Next, an ultraviolet absorption portion was scraped off, and extracted with the developing solvent, and thereafter the extract was concentrated to dryness, to give 57.2 mg of a yellow substance.

(2) The NMR spectra and the mass spectrum of the yellow substance obtained in item (1) of Example 8 were determined in the same manner as in item (6) of Example 1. The signals of NMR are shown below. In addition, the numbers of the peaks are shown in the following formula (Ka 18).

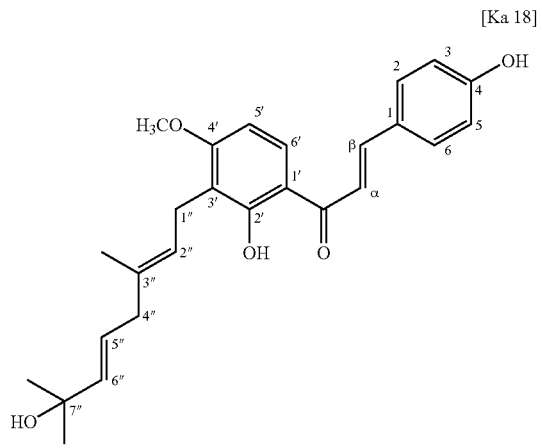

[Ka 18]

$^1$H-NMR (deuterated dimethyl sulfoxide): δ1.13 (3H, s, CH$_3$-7''), 1.13 (3H, s, CH$_3$-7''), 1.70 (3H, s, CH$_3$-3''), 2.59 (2H, d, J=7.2 Hz, H-4''), 3.28 (2H, d, J=7.2 Hz, H-1''), 3.91 (3H, s, OCH$_3$-4'), 4.42 (1H, s, OH-7''), 5.17 (1H, t, J=7.2 Hz, H-2''), 5.42 (1H, m, H-5''), 5.52 (1H, d, J=15.0 Hz, H-6''), 6.68 (1H, d, J=9.0 Hz, H-5'), 6.85 (2H, d, J=9.0 Hz, H-3 and H-5), 7.77 (1H, d, J=15.0 Hz, H-β), 7.78 (2H, d, J=9.0 Hz, H-2 and H-6), 7.83 (1H, d, J=15.0 Hz, H-α), 8.24 (1H, d, J=9.0 Hz, H-6'), 10.17 (1H, s, OH-4), 13.80 (1H, s, OH-2')

FIG. 15 shows $^1$H-NMR spectrum.

$^{13}$C-NMR (deuterated dimethyl sulfoxide): δ16.8 (CH$_3$-3''), 22.1 (C-1''), 31.0 (CH$_3$-7''), 31.0 (CH$_3$-7''), 42.7 (C-4''), 56.9 (OCH$_3$-4'), 69.7 (C-7''), 103.6 (C-5'), 114.9 (C-1'), 116.7 (C-3'), 116.7 (C-3 and C-5), 118.1 (C-α), 123.2 (C-2''), 123.9 (C-5''), 126.6 (C-1), 131.3 (C-6'), 132.3 (C-2 and C-6), 134.6 (C-3''), 141.5 (C-6''), 145.7 (C-β), 161.3 (C-4), 163.0 (C-2'), 163.8 (C-4'), 193.3 (C=O)

FIG. 16 shows $^{13}$C-NMR spectrum.

FAB-MS: m/z 421(M-H)$^-$: Metanitrobenzyl alcohol was used as the matrix.

From the above results of the NMR spectrum analysis and mass spectrum analysis, the yellow substance obtained in item (1) of Example 8 was identified to be 1-[2-hydroxy-3-(7-hydroxy-3,7-dimethyl-2,5-octadienyl)-4-methoxyphenyl]-3-(4-hydroxyphenyl)-2-propen-1-one (molecular weight: 422, compound (C081)).

Example 9

Preparation of Compound (C042)

(1) 2',4'-Dihydroxyacetophenone (manufactured by Wako Pure Chemical Industries, Ltd.) was treated with 1-bromo-2-methyl-2-butene (manufactured by Aldrich) in 2 M KOH/methanol solution under ice-cooling, and thereafter the treated solution was hydrogenated in methanol, in the presence of palladium black (manufactured by Nakalai Tesque, Inc.), to give 2',4'-dihydroxy-3'-(3-methylbutyl)acetophenone. Subsequently, 2',4'-dihydroxy-3'-(3-methylbutyl)acetophenone and 4-hydroxybenzaldehyde (manufactured by Aldrich) were subjected to Claisen condensation, to give a yellow substance.

(2) The NMR spectra and the mass spectrum of the yellow substance obtained in item (1) of Example 9 were determined in the same manner as in item (6) of Example 1. The signals of NMR are shown below. In addition, the numbers of the peaks are shown in the following formula (Ka 19).

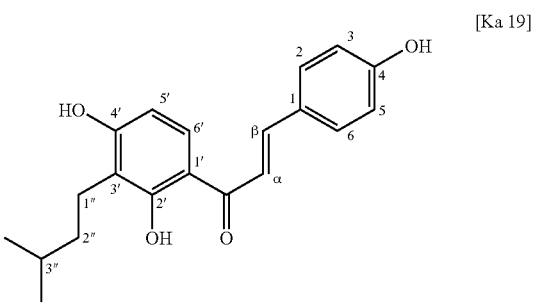

[Ka 19]

$^1$H-NMR (deuterated dimethyl sulfoxide): δ0.91 (3H, s, CH$_3$-3''), 0.92 (3H, s, CH$_3$-3''), 1.34 (2H, m, H-2''), 1.54 (1H, m, H-3''), 2.55 (2H, m, H-1''), 6.47 (1H, d, J=9.0 Hz, H-5'), 6.84 (2H, d, J=9.0 Hz, H-3 and H-5), 7.74 (2H, d, J=9.0 Hz, H-2 and H-6), 7.74 (2H, s, H-α, H-β), 8.02 (1H, d, J=9.0 Hz, H-6'), 10.10 (1H, s, OH-4), 10.46 (1H, s, OH-4') 13.98 (1H, s, OH-2')

FIG. 17 shows $^1$H-NMR spectrum.

FAB-MS: m/z 327(M+H)$^+$: Metanitrobenzyl alcohol was used as the matrix.

From the above results of the NMR spectrum analysis and mass spectrum analysis, the yellow substance obtained in item (1) of Example 9 was identified to be 1-[2,4-dihydroxy-3-(3-methylbutyl)phenyl]-3-(4-hydroxyphenyl)-2-propen-1-one (molecular weight: 326, compound (C042)).

Example 10

Inhibitory Activities of Aldose Reductase

Inhibitory activities of aldose reductase of the compounds prepared in Examples 1 to 9 (TB3, TB4, TB5, TB6, TB7, TB8, TB9, compound (C081) or compound (C042)) were measured by the following method. Twenty microliters of 100 mM methylglyoxal was added to 10 μL of a sample (dissolved each compound in a 50% aqueous dimethyl sulfoxide solution), 100 μL of 0.2 M phosphate buffer (pH 6.2), 20 μL of 1 mM NADPH (phosphate buffer), and 10 μL of a solution of aldose reductase derived from human muscle cells (0.1 U/mL, manufactured by Wako Pure Chemical Industries, phosphate buffer). After 30 seconds passed, change in absorbance of NADPH at 340 nm was determined for 180 seconds. A 50% aqueous dimethyl sulfoxide solution was used as a negative control in place of the sample. In addition, the absorbance was determined using distilled water as a blank of each sample in place of the methylglyoxal solution. The found values are expressed as an average of the values in two experimental values. The inhibitory ratio (%) of aldose reductase was calculated in accordance with the following formula.

Inhibitory Ratio (%)=[1−[(ΔAs−ΔAsb)/(ΔAc−ΔAcb)]]×100

Here, ΔAs and ΔAc are changes in absorbance per 1 minute of a sample solution, and a negative control solution, respectively, and ΔAsb and ΔAcb are changes in absorbance per 1 minute of blank of a sample solution, and a negative control solution, respectively.

The amount of the sample is so that a final concentration of each compound is as shown in Table 1. As a result, it was revealed that TB3, TB4, TB5, TB6, TB7, TB8, TB9, compound (C081) and compound (C042) have inhibitory activities of aldose reductase in a concentration-dependent manner. The results are shown in Table 1.

TABLE 1

| Compound | Inhibitory Ratio (%) of Aldose Reductase Concentration | | |
|---|---|---|---|
| | 10 μM | 20 μM | 40 μM |
| TB3 | 14.2 | 30.1 | 53.8 |
| TB4 | 57.4 | 57.9 | N.T. |
| TB5 | 35.1 | 49.7 | 66.7 |
| TB6 | 41.9 | 56.5 | 66.8 |
| TB7 | 20.1 | 33.8 | 54.3 |
| TB8 | 17.9 | 32.7 | 44.2 |
| TB9 | 31.6 | 44.7 | 57.3 |
| Compound (C081) | 11.9 | 16.2 | 26.7 |
| Compound (C042) | 47.8 | 68.7 | N.T. |

N.T.: Not tested.

Example 11

Suppressive Activities of NO Production

Suppressive activities of NO production of the compounds prepared in Examples 1 to 9 (TB3, TB4, TB5, TB6, TB7, TB8, TB9, compound (C081) and compound (C042)) were measured by the following method. RAW 264.7 cells (ATCC TIB 71) were suspended in Dulbecco's modified Eagle's medium (manufactured by Sigma, D5796) containing 10% fetal bovine serum (manufactured by Bio Whittaker, 14-506F), so as to have a concentration of $4 \times 10^5$ cells/mL, and the suspension was put to each well of a 48-well microtiter plate in an amount of 500 μL per well. The cells were cultured at 37° C. in the presence of 5% carbon dioxide gas. After 24 hours, the medium was exchanged with Dulbecco's modified Eagle's medium (manufactured by Bio Whittaker, 12-917F) containing 10% fetal bovine serum (manufactured by Bio Whittaker), 2 mM L-glutamine (manufactured by Life Tech Oriental Co., Ltd., 25030-149) without containing phenol red. A 10 mM, 5 mM, or 2.5 mM TB3, TB4, TB5, TB6, TB7, TB8, TB9, compound (C081) or compound (C042) (all are dimethyl sulfoxide solution) was added to each well in an amount of 1 μL per well. After additional 1 hour of culture, a 100 μg/mL aqueous lipopolysaccharide (LPS, manufactured by Sigma, L-2010) solution was added to each well in an amount of 5 μL per well, and the cells were cultured for 16 hours. Thereafter, the concentration of $NO_2^-$ which was produced by oxidation of NO in the medium was determined. In addition, there was set a group with addition of dimethyl sulfoxide in place of the each compound as a control. After the above-mentioned culture, 100 μL of a 4% grease reagent (manufactured by Sigma, G4410) was added to 100 μL of the supernatant of the culture medium, and the mixture was allowed to stand at room temperature for 15 minutes. Thereafter, absorbance at 540 nm was determined. The concentration of $NO_2^-$ in the medium was calculated from a calibration curve prepared from known concentrations of $NaNO_2$ (manufactured by Sigma, S2252). All of the determinations were carried out twice. The suppressive ability of NO production of the each compound was calculated in accordance with the following formula.

X: Amount of $NO_2^-$ in the presence of each compound

Y: Amount of $NO_2^-$ in a control

Suppressive Ability of NO Production (%)=[1−$X/Y$]×100

As a result, TB3, TB4, TB5, TB6, TB7, TB8, TB9, compound (C081) and compound (C042) suppressed the induction of NO production by LPS in a concentration-dependent manner. The results are shown in Table 2.

TABLE 2

| Compound | Suppressive Ability for Induction of NO Production by LPS (%) Concentration | | |
|---|---|---|---|
| | 5 μM | 10 μM | 20 μM |
| TB3 | 8.9 | 9.5 | 43.8 |
| TB4 | 32.6 | 56.4 | 63.7 |
| TB5 | 17.9 | 35.2 | 76.0 |
| TB6 | 17.3 | 29.4 | 62.2 |
| TB7 | 12.2 | 23.9 | 42.9 |
| TB8 | 12.2 | 18.7 | 36.9 |
| TB9 | 11.2 | 29.2 | 49.6 |
| Compound (C081) | N.T. | 31.6 | 53.7 |
| Compound (C042) | N.T. | 19.3 | 50.2 |

N.T.: Not tested.

INDUSTRIAL APPLICABILITY

According to the present invention, there is provided a novel chalcone compound. The compound has its suppressive action of NO production or its inhibitory action of aldose reductase, so that the compound is useful as an effective ingredient of a medicament, a food, a beverage or a feed, each utilizing the physiological activities.

We claim:
1. A chalcone compound represented by any one of the following formulas (1) to (8) or a salt thereof:
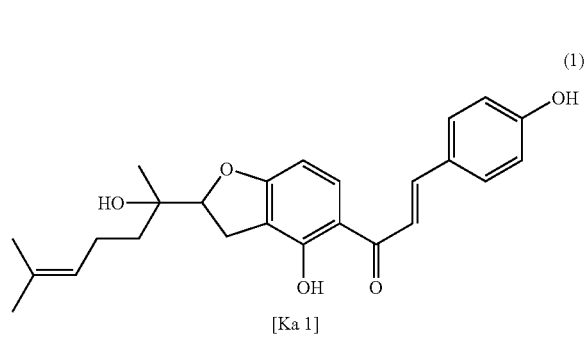
[Ka 1]    (1)
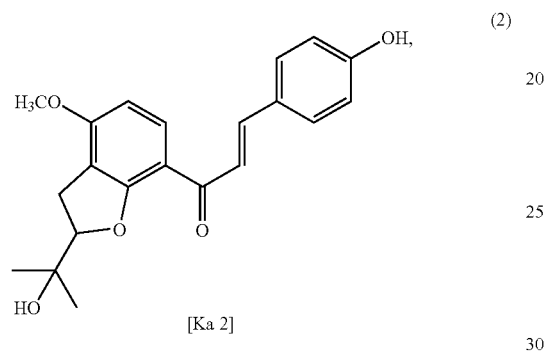
[Ka 2]    (2)
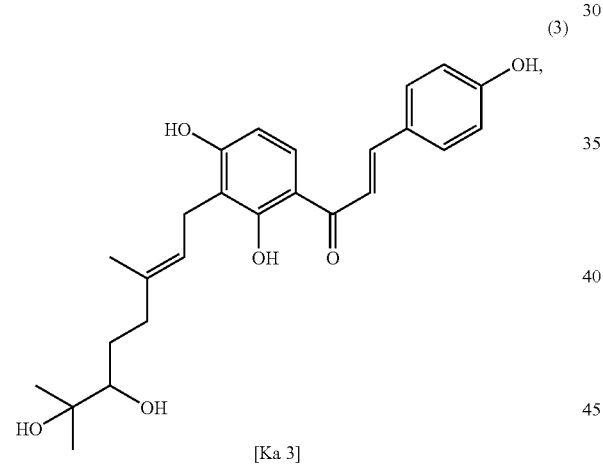
[Ka 3]    (3)
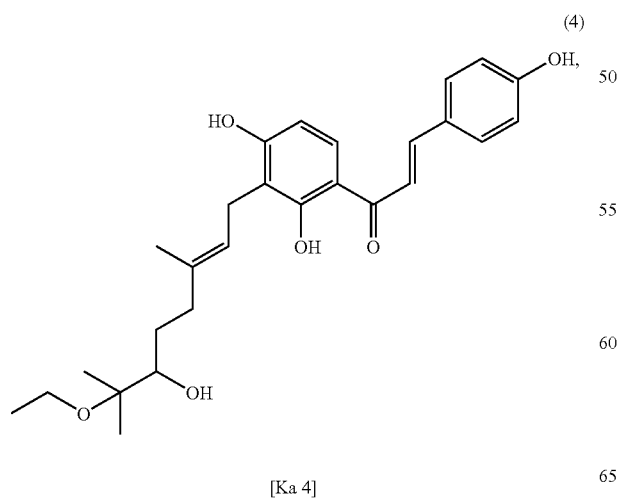
[Ka 4]    (4)
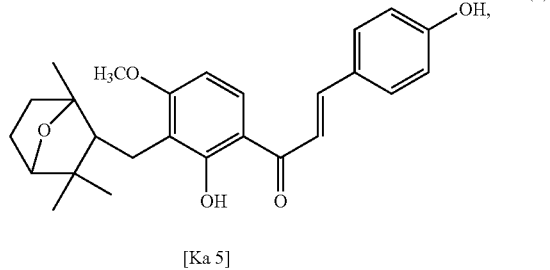
[Ka 5]    (5)
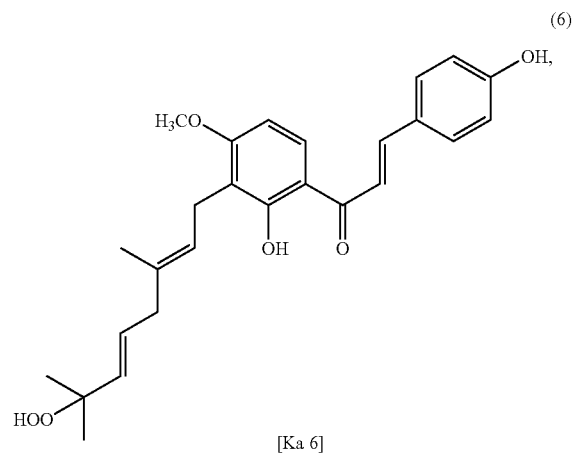
[Ka 6]    (6)
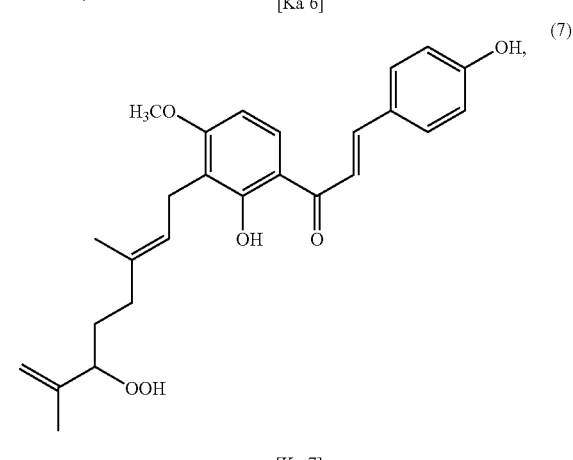
[Ka 7]    (7)
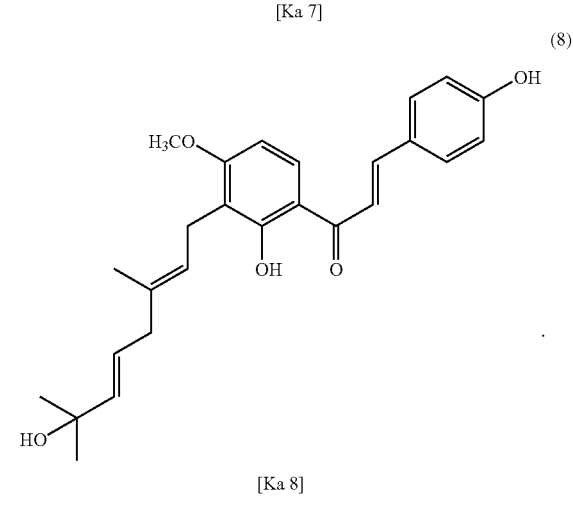
[Ka 8]    (8)

2. A therapeutic agent comprising the compound or a salt thereof according to claim 1.

3. A food, beverage or feed, comprising the compound or a salt thereof according to claim 1.

4. The compound according to claim 1, which is an ester thereof or an ether thereof, or comprises a hydrolyzable glycoside, or a salt thereof.

5. A method of treating a subject in need thereof, which comprises administering an effective amount of a compound according to claim 1 to a subject in need thereof, wherein said subject in need thereof suffers from one or more diseases or afflictions selected from the group consisting of: carcinogenetic diseases, inflammatory diseases, chronic rheumatic arthritis, rheumatic osteoarthritis, gouty arthritis, Behcet's disease, cataracts, peripheral nerve disease, nephritic disease, infections caused by lowering of phagocytotic action of leukocytes, diabetic coma, and arteriosclerosis caused by atheromatous degeneration in the great vessel wall.

6. The method according to claim 5, wherein an amount of the compound administered is from 10 μg/g to 100 mg/kg of body weight of the subject.

* * * * *